(12) United States Patent
Girouard et al.

(10) Patent No.: US 7,840,263 B2
(45) Date of Patent: *Nov. 23, 2010

(54) METHOD AND APPARATUS FOR DEVICE CONTROLLED GENE EXPRESSION

(75) Inventors: Steven D. Girouard, Woodbury, MN (US); Jeffrey Ross, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/788,906

(22) Filed: Feb. 27, 2004

(65) Prior Publication Data

US 2005/0192637 A1 Sep. 1, 2005

(51) Int. Cl.
*A61N 1/02* (2006.01)

(52) U.S. Cl. .......................................................... 607/3

(58) Field of Classification Search ............. 607/4, 607/5, 9, 1–3; 604/19–21
See application file for complete search history.

(56) References Cited

U.S. PATENT DOCUMENTS

| | | | |
|---|---|---|---|
| 3,692,027 A | 9/1972 | Ellinwood, Jr. |
| 4,003,379 A | 1/1977 | Ellinwood, Jr. |
| 4,146,029 A | 3/1979 | Ellinwood, Jr. |
| 4,281,664 A | 8/1981 | Duggan |
| 4,299,220 A | 11/1981 | Dorman |
| 4,544,371 A | 10/1985 | Dormandy, Jr. et al. |
| 4,556,063 A | 12/1985 | Thompson et al. |
| 4,677,989 A | 7/1987 | Robblee |
| 4,686,987 A | 8/1987 | Salo et al. |
| 4,871,351 A | 10/1989 | Feingold |
| 4,897,987 A | 2/1990 | Spalla |
| 4,902,508 A | 2/1990 | Badylak et al. |
| 4,924,875 A | 5/1990 | Chamoun |
| 4,938,231 A | 7/1990 | Milijasevic et al. |
| 4,944,299 A | 7/1990 | Silvian |
| 4,987,897 A | 1/1991 | Funke |

(Continued)

FOREIGN PATENT DOCUMENTS

EP 0054138 6/1982

(Continued)

OTHER PUBLICATIONS

"Invitation to Pay Additional Fees and Partial International Search Report, for Application No. PCT/US2005/006069, date mailed Jul. 20, 2005", 7 Pages.

(Continued)

*Primary Examiner*—Carl H. Layno
*Assistant Examiner*—Jessica Sarcione
(74) *Attorney, Agent, or Firm*—Schwegman, Lundberg & Woessner, P.A.

(57) ABSTRACT

A gene regulatory system controls gene therapy by emitting one or more forms of energy that regulate gene expression by triggering promoters. The system includes a sensor to sense a signal indicative of a need for the gene therapy as well as responses to the gene therapy. The regulation of the gene expression is controlled based on the sensed signal and/or a user command. In one embodiment, the system delivers one or more electrical therapies in conjunction with the gene therapy.

77 Claims, 3 Drawing Sheets

U.S. PATENT DOCUMENTS

| | | |
|---|---|---|
| 5,014,698 A | 5/1991 | Cohen |
| 5,025,786 A | 6/1991 | Siegel |
| 5,031,621 A | 7/1991 | Grandjean et al. |
| 5,040,533 A | 8/1991 | Fearnot |
| 5,041,107 A | 8/1991 | Heil, Jr. |
| 5,042,497 A | 8/1991 | Shapland |
| 5,058,581 A | 10/1991 | Silvian |
| 5,087,243 A | 2/1992 | Avitall |
| 5,103,821 A | 4/1992 | King |
| 5,109,842 A | 5/1992 | Adinolfi |
| 5,127,404 A | 7/1992 | Wyborny et al. |
| 5,130,141 A | 7/1992 | Law et al. |
| 5,156,572 A | 10/1992 | Morishige |
| 5,179,947 A | 1/1993 | Meyerson et al. |
| 5,190,035 A | 3/1993 | Salo et al. |
| 5,220,917 A | 6/1993 | Cammilli et al. |
| 5,251,621 A | 10/1993 | Collins |
| 5,259,380 A | 11/1993 | Mendes et al. |
| 5,269,301 A | 12/1993 | Cohen |
| 5,275,826 A | 1/1994 | Badylak et al. |
| 5,284,136 A | 2/1994 | Hauck et al. |
| 5,305,745 A | 4/1994 | Zacouto |
| 5,312,453 A * | 5/1994 | Shelton et al. ................. 607/19 |
| 5,314,430 A * | 5/1994 | Bardy ........................... 607/5 |
| 5,336,252 A | 8/1994 | Cohen |
| 5,342,408 A | 8/1994 | deCoriolis et al. |
| 5,347,241 A | 9/1994 | Panaretos et al. |
| 5,352,463 A | 10/1994 | Badylak et al. |
| 5,353,800 A | 10/1994 | Pohndorf et al. |
| 5,354,264 A | 10/1994 | Bae et al. |
| 5,368,028 A | 11/1994 | Palti |
| 5,387,419 A | 2/1995 | Levy et al. |
| 5,404,877 A | 4/1995 | Nolan et al. |
| 5,409,009 A | 4/1995 | Olson |
| 5,416,695 A | 5/1995 | Stutman et al. |
| 5,423,883 A | 6/1995 | Helland |
| 5,435,999 A | 7/1995 | Austin |
| 5,456,692 A | 10/1995 | Smith, Jr. et al. |
| 5,460,605 A | 10/1995 | Tuttle et al. |
| 5,486,359 A | 1/1996 | Caplan et al. |
| 5,496,360 A | 3/1996 | Hoffmann et al. |
| 5,499,971 A | 3/1996 | Shapland et al. |
| 5,507,724 A | 4/1996 | Hofmann et al. |
| 5,509,924 A | 4/1996 | Paspa et al. |
| 5,538,722 A | 7/1996 | Blau et al. |
| 5,543,318 A | 8/1996 | Smith et al. |
| 5,551,953 A | 9/1996 | Lattin et al. |
| 5,554,389 A | 9/1996 | Badylak et al. |
| 5,556,421 A | 9/1996 | Prutchi et al. |
| 5,558,632 A | 9/1996 | Lloyd et al. |
| 5,562,713 A | 10/1996 | Silvian |
| 5,571,151 A | 11/1996 | Gregory |
| 5,579,876 A | 12/1996 | Adrian et al. |
| 5,580,779 A | 12/1996 | Smith et al. |
| 5,586,556 A | 12/1996 | Spivey et al. |
| 5,602,301 A | 2/1997 | Field |
| 5,603,331 A | 2/1997 | Heemels et al. |
| 5,607,418 A | 3/1997 | Arzbaecher |
| 5,609,629 A | 3/1997 | Fearnot et al. |
| 5,610,172 A | 3/1997 | Weidmann et al. |
| 5,634,899 A | 6/1997 | Shapland et al. |
| 5,662,689 A | 9/1997 | Elsberry et al. |
| 5,681,735 A | 10/1997 | Emerson et al. |
| 5,690,682 A | 11/1997 | Buscemi et al. |
| 5,693,075 A | 12/1997 | Plicchi et al. |
| 5,703,125 A | 12/1997 | Bovy et al. |
| 5,704,908 A | 1/1998 | Hofmann et al. |
| 5,720,770 A | 2/1998 | Nappholz et al. |
| 5,730,125 A | 3/1998 | Prutchi et al. |
| 5,733,727 A | 3/1998 | Field |
| 5,741,319 A | 4/1998 | Woloszko et al. |
| 5,800,498 A | 9/1998 | Obino et al. |
| 5,807,306 A | 9/1998 | Shapland et al. |
| 5,817,131 A | 10/1998 | Elsberry et al. |
| 5,824,049 A | 10/1998 | Ragheb et al. |
| 5,833,603 A | 11/1998 | Kovacs et al. |
| 5,833,978 A | 11/1998 | Tremblay |
| 5,834,029 A | 11/1998 | Bellamkonda et al. |
| 5,836,935 A | 11/1998 | Ashton et al. |
| 5,849,033 A | 12/1998 | Mehmanesh et al. |
| 5,855,610 A | 1/1999 | Vacanti et al. |
| 5,865,787 A | 2/1999 | Shapland et al. |
| 5,873,904 A | 2/1999 | Ragheb et al. |
| 5,885,797 A | 3/1999 | Chen et al. |
| 5,893,881 A | 4/1999 | Elsberry et al. |
| 5,899,928 A | 5/1999 | Sholder et al. |
| 5,902,324 A * | 5/1999 | Thompson et al. ............. 607/9 |
| 5,914,242 A | 6/1999 | Honkanen et al. |
| 5,925,066 A | 7/1999 | Kroll et al. |
| 5,928,943 A | 7/1999 | Franz et al. |
| 5,944,710 A | 8/1999 | Dev et al. |
| 5,945,577 A | 8/1999 | Stice et al. |
| 5,949,659 A | 9/1999 | Lesche |
| 5,967,986 A | 10/1999 | Cimochowski et al. |
| 5,968,006 A | 10/1999 | Hofmann |
| 5,991,668 A | 11/1999 | Leinders et al. |
| 6,005,009 A | 12/1999 | Murad et al. |
| 6,016,447 A | 1/2000 | Juran et al. |
| 6,016,448 A | 1/2000 | Busacker et al. |
| 6,048,722 A | 4/2000 | Farb et al. |
| 6,050,980 A | 4/2000 | Wilson |
| 6,059,726 A | 5/2000 | Lee et al. |
| 6,066,094 A | 5/2000 | Ben-Haim |
| 6,083,930 A | 7/2000 | Roufa et al. |
| 6,090,622 A | 7/2000 | Gearhart et al. |
| 6,096,070 A | 8/2000 | Ragheb et al. |
| 6,096,347 A | 8/2000 | Geddes et al. |
| 6,099,832 A | 8/2000 | Mickle et al. |
| 6,100,242 A | 8/2000 | Hammond |
| 6,108,577 A | 8/2000 | Benser |
| 6,110,459 A | 8/2000 | Mickle et al. |
| 6,112,116 A | 8/2000 | Fischell et al. |
| 6,114,164 A | 9/2000 | Dennis et al. |
| 6,115,636 A | 9/2000 | Ryan |
| 6,117,296 A | 9/2000 | Thomson |
| 6,128,526 A | 10/2000 | Stadler et al. |
| 6,132,419 A | 10/2000 | Hofmann |
| 6,135,976 A | 10/2000 | Tachibana et al. |
| 6,140,740 A | 10/2000 | Porat et al. |
| 6,151,525 A | 11/2000 | Soykan et al. |
| 6,152,955 A | 11/2000 | KenKnight et al. |
| 6,154,675 A | 11/2000 | Juran et al. |
| 6,155,267 A | 12/2000 | Nelson |
| 6,165,164 A | 12/2000 | Hill et al. |
| 6,168,801 B1 | 1/2001 | Heil, Jr. et al. |
| 6,174,871 B1 | 1/2001 | Hammond et al. |
| 6,184,030 B1 | 2/2001 | Katoot et al. |
| 6,185,461 B1 | 2/2001 | Er |
| 6,198,394 B1 | 3/2001 | Jacobsen et al. |
| 6,199,554 B1 | 3/2001 | Mann et al. |
| 6,200,265 B1 | 3/2001 | Walsh et al. |
| 6,203,495 B1 | 3/2001 | Bardy |
| 6,206,914 B1 | 3/2001 | Soykan et al. |
| 6,207,451 B1 | 3/2001 | Dennis et al. |
| 6,213,942 B1 | 4/2001 | Flach et al. |
| 6,221,011 B1 | 4/2001 | Bardy |
| 6,224,566 B1 | 5/2001 | Loeb |
| 6,231,516 B1 | 5/2001 | Keilman et al. |
| 6,235,970 B1 | 5/2001 | Stice et al. |
| 6,237,398 B1 | 5/2001 | Porat et al. |
| 6,245,566 B1 | 6/2001 | Gearhart et al. |
| 6,254,573 B1 | 7/2001 | Haim et al. |
| 6,256,233 B1 | 7/2001 | Glass |
| 6,261,230 B1 | 7/2001 | Bardy |

| | | | | | |
|---|---|---|---|---|---|
| 6,270,457 B1 | 8/2001 | Bardy | 6,748,653 B2 | 6/2004 | Lindemans et al. |
| 6,277,072 B1 | 8/2001 | Bardy | 6,759,236 B2 | 7/2004 | Fung et al. |
| 6,277,078 B1 | 8/2001 | Porat et al. | 6,775,569 B2 | 8/2004 | Mori et al. |
| 6,280,380 B1 | 8/2001 | Bardy | 6,775,574 B1 | 8/2004 | Soykan et al. |
| 6,284,242 B1 | 9/2001 | Kurachi | 6,801,805 B2 | 10/2004 | Stokes et al. |
| 6,287,285 B1 | 9/2001 | Michal et al. | 6,810,286 B2 | 10/2004 | Donovan et al. |
| 6,298,272 B1 | 10/2001 | Peterfeso et al. | 6,855,124 B1 | 2/2005 | Gonzalez et al. |
| 6,306,830 B1 | 10/2001 | Hammond et al. | 6,865,420 B1 * | 3/2005 | Kroll .................... 607/25 |
| 6,309,370 B1 | 10/2001 | Haim et al. | 6,902,522 B1 | 6/2005 | Walsh et al. |
| 6,312,378 B1 | 11/2001 | Bardy | 6,905,476 B2 | 6/2005 | Ponzi |
| 6,316,419 B1 | 11/2001 | Leiden et al. | 6,919,207 B2 | 7/2005 | Goodman et al. |
| 6,330,481 B1 | 12/2001 | Van Wijk et al. | 6,965,798 B2 | 11/2005 | Kim |
| 6,331,160 B1 | 12/2001 | Bardy | 6,969,382 B2 | 11/2005 | Richter |
| 6,336,903 B1 | 1/2002 | Bardy | 6,973,349 B2 | 12/2005 | Salo |
| 6,358,202 B1 | 3/2002 | Arent | 6,976,982 B2 | 12/2005 | Santini, Jr. et al. |
| 6,358,203 B2 | 3/2002 | Bardy | 7,039,462 B2 | 5/2006 | Pastore et al. |
| 6,361,522 B1 | 3/2002 | Scheiner et al. | 7,072,711 B2 * | 7/2006 | Girouard et al. ............ 607/3 |
| 6,361,780 B1 | 3/2002 | Ley et al. | 7,294,334 B1 | 11/2007 | Michal et al. |
| 6,368,284 B1 | 4/2002 | Bardy | 7,621,906 B2 | 11/2009 | Pastore et al. |
| 6,385,491 B1 | 5/2002 | Lindemans et al. | 7,627,373 B2 | 12/2009 | Girouard et al. |
| 6,387,369 B1 | 5/2002 | Pittenger et al. | 7,729,761 B2 | 6/2010 | Girouard et al. |
| 6,388,043 B1 | 5/2002 | Langer et al. | 2001/0000802 A1 | 5/2001 | Soykan et al. |
| 6,398,728 B1 | 6/2002 | Bardy | 2001/0016193 A1 | 8/2001 | Engler |
| 6,399,300 B1 | 6/2002 | Field | 2001/0041928 A1 | 11/2001 | Pavcnik et al. |
| 6,410,236 B1 | 6/2002 | Metzger | 2001/0051148 A1 | 12/2001 | Tremblay |
| 6,411,840 B1 | 6/2002 | Bardy | 2001/0055590 A1 | 12/2001 | Kurachi |
| 6,424,847 B1 | 7/2002 | Mastrototaro et al. | 2002/0001577 A1 | 1/2002 | Haverich et al. |
| 6,428,802 B1 | 8/2002 | Atala | 2002/0010492 A1 | 1/2002 | Donovan et al. |
| 6,436,672 B1 | 8/2002 | Tomlinson | 2002/0012657 A1 | 1/2002 | Tremblay |
| 6,436,907 B1 | 8/2002 | Leiden et al. | 2002/0019350 A1 * | 2/2002 | Levine et al. ............... 514/12 |
| 6,440,066 B1 | 8/2002 | Bardy | 2002/0022259 A1 | 2/2002 | Lee et al. |
| 6,443,949 B2 | 9/2002 | Altman | 2002/0031501 A1 | 3/2002 | Law |
| 6,451,594 B1 | 9/2002 | Chien et al. | 2002/0031827 A1 | 3/2002 | Kanno et al. |
| 6,453,195 B1 | 9/2002 | Thompson | 2002/0032468 A1 | 3/2002 | Hill et al. |
| 6,459,917 B1 | 10/2002 | Gowda et al. | 2002/0035346 A1 | 3/2002 | Reynolds et al. |
| 6,459,929 B1 | 10/2002 | Hopper et al. | 2002/0048800 A1 | 4/2002 | Gu et al. |
| 6,463,323 B1 | 10/2002 | Conrad-Vlasak et al. | 2002/0049154 A1 | 4/2002 | Grissom et al. |
| 6,463,335 B1 | 10/2002 | Munch et al. | 2002/0055530 A1 | 5/2002 | Neuberger et al. |
| 6,468,263 B1 | 10/2002 | Fischell et al. | 2002/0055705 A1 | 5/2002 | Talpade et al. |
| 6,468,985 B1 | 10/2002 | Huang | 2002/0065243 A1 | 5/2002 | Fung et al. |
| 6,475,232 B1 | 11/2002 | Babbs et al. | 2002/0072785 A1 | 6/2002 | Nelson et al. |
| 6,478,737 B2 | 11/2002 | Bardy | 2002/0077311 A1 | 6/2002 | Leiden et al. |
| 6,490,482 B2 | 12/2002 | Mori et al. | 2002/0098167 A1 | 7/2002 | Anversa et al. |
| 6,501,983 B1 | 12/2002 | Natarajan et al. | 2002/0099026 A1 | 7/2002 | Goodman et al. |
| 6,507,756 B1 | 1/2003 | Heynen et al. | 2002/0107553 A1 | 8/2002 | Hill et al. |
| 6,511,477 B2 | 1/2003 | Altman et al. | 2002/0110910 A1 | 8/2002 | Gwathmey et al. |
| 6,518,245 B1 | 2/2003 | Anderson et al. | 2002/0115208 A1 | 8/2002 | Mitchell et al. |
| 6,540,725 B1 | 4/2003 | Ponzi | 2002/0124855 A1 | 9/2002 | Chachques |
| 6,541,116 B2 | 4/2003 | Michal et al. | 2002/0127210 A1 | 9/2002 | Mickle et al. |
| 6,571,125 B2 | 5/2003 | Thompson | 2002/0133198 A1 | 9/2002 | Kramer et al. |
| 6,574,507 B1 | 6/2003 | Bonnet | 2002/0142457 A1 | 10/2002 | Umezawa et al. |
| 6,575,931 B1 | 6/2003 | Ponzi | 2002/0147172 A1 | 10/2002 | Podsakoff et al. |
| 6,592,623 B1 | 7/2003 | Bowlin et al. | 2002/0147329 A1 | 10/2002 | Luyten et al. |
| 6,596,745 B2 | 7/2003 | Gall | 2002/0155101 A1 * | 10/2002 | Donahue et al. ......... 424/93.21 |
| 6,610,716 B2 | 8/2003 | Wagle et al. | 2002/0161410 A1 | 10/2002 | Kramer et al. |
| 6,623,473 B1 | 9/2003 | Ponzi | 2002/0165191 A1 | 11/2002 | Moonen |
| 6,623,474 B1 | 9/2003 | Ponzi | 2002/0172663 A1 | 11/2002 | Palasis |
| 6,628,987 B1 | 9/2003 | Hill et al. | 2002/0183682 A1 | 12/2002 | Darvish et al. |
| 6,628,988 B2 | 9/2003 | Kramer et al. | 2002/0183686 A1 * | 12/2002 | Darvish et al. ............... 604/21 |
| 6,653,291 B1 | 11/2003 | Badylak et al. | 2002/0183720 A1 | 12/2002 | Hill et al. |
| 6,654,636 B1 | 11/2003 | Dev et al. | 2003/0004403 A1 | 1/2003 | Drinan et al. |
| 6,656,517 B2 | 12/2003 | Michal | 2003/0026784 A1 | 2/2003 | Koch et al. |
| 6,660,737 B2 | 12/2003 | Almstead et al. | 2003/0036773 A1 | 2/2003 | Whitehurst et al. |
| 6,662,044 B2 | 12/2003 | Crawford et al. | 2003/0036801 A1 | 2/2003 | Schwartz et al. |
| 6,666,826 B2 | 12/2003 | Salo et al. | 2003/0040777 A1 | 2/2003 | Shemer et al. |
| 6,671,558 B1 | 12/2003 | Soykan et al. | 2003/0044802 A1 | 3/2003 | Sayler et al. |
| 6,678,556 B1 | 1/2004 | Nolan et al. | 2003/0045830 A1 | 3/2003 | de Bizemont et al. |
| 6,689,117 B2 | 2/2004 | Sweeney et al. | 2003/0059463 A1 | 3/2003 | Lahtinen |
| 6,690,970 B1 | 2/2004 | Taheri et al. | 2003/0060854 A1 | 3/2003 | Zhu |
| 6,697,669 B2 | 2/2004 | Dev et al. | 2003/0060857 A1 | 3/2003 | Perrson et al. |
| 6,702,777 B2 | 3/2004 | Haim et al. | 2003/0065379 A1 | 4/2003 | Babbs et al. |
| 6,733,996 B2 | 5/2004 | Froehlich et al. | 2003/0073235 A1 | 4/2003 | Lagarias et al. |
| 6,735,471 B2 | 5/2004 | Hill et al. | 2003/0082148 A1 | 5/2003 | Ludwig et al. |

| | | |
|---|---|---|
| 2003/0087264 A1* | 5/2003 | Kaplitt et al. ............... 435/6 |
| 2003/0087867 A1 | 5/2003 | Vogels et al. |
| 2003/0104568 A1 | 6/2003 | Lee |
| 2003/0105493 A1 | 6/2003 | Salo |
| 2003/0113303 A1 | 6/2003 | Schwartz |
| 2003/0125615 A1 | 7/2003 | Schwartz |
| 2003/0129750 A1 | 7/2003 | Schwartz |
| 2003/0130581 A1 | 7/2003 | Salo et al. |
| 2003/0138415 A1 | 7/2003 | Shepard |
| 2003/0144702 A1 | 7/2003 | Yu et al. |
| 2003/0144703 A1 | 7/2003 | Yu et al. |
| 2003/0148351 A1 | 8/2003 | Henry et al. |
| 2003/0148968 A1 | 8/2003 | Hammond et al. |
| 2003/0153952 A1 | 8/2003 | Auricchio et al. |
| 2003/0167081 A1 | 9/2003 | Zhu et al. |
| 2003/0171723 A1 | 9/2003 | Ponzi |
| 2003/0187396 A1 | 10/2003 | Ponzi |
| 2003/0187490 A1 | 10/2003 | Gliner |
| 2003/0195470 A1 | 10/2003 | Ponzi |
| 2003/0199813 A1* | 10/2003 | Struble ............... 604/66 |
| 2003/0204206 A1 | 10/2003 | Padua et al. |
| 2003/0211130 A1 | 11/2003 | Sanders et al. |
| 2003/0216476 A1 | 11/2003 | Kleemann |
| 2003/0216811 A1 | 11/2003 | Badylak |
| 2003/0216812 A1 | 11/2003 | Badylak |
| 2004/0002739 A1 | 1/2004 | Cates et al. |
| 2004/0006395 A1 | 1/2004 | Badylak |
| 2004/0014052 A1 | 1/2004 | Kurtz et al. |
| 2004/0018174 A1 | 1/2004 | Palasis |
| 2004/0030379 A1* | 2/2004 | Hamm et al. ............. 623/1.15 |
| 2004/0038400 A1 | 2/2004 | Froehlich et al. |
| 2004/0043006 A1 | 3/2004 | Badylak et al. |
| 2004/0047909 A1 | 3/2004 | Ragheb et al. |
| 2004/0048286 A1 | 3/2004 | Lee |
| 2004/0071637 A1 | 4/2004 | Elia |
| 2004/0073260 A1* | 4/2004 | Brighton ............... 607/2 |
| 2004/0087019 A1 | 5/2004 | Soykan et al. |
| 2004/0088017 A1* | 5/2004 | Sharma et al. ............. 607/25 |
| 2004/0098075 A1 | 5/2004 | Lee |
| 2004/0122478 A1* | 6/2004 | Stadler et al. ............. 607/17 |
| 2004/0131601 A1 | 7/2004 | Epstein et al. |
| 2004/0132184 A1 | 7/2004 | Dennis et al. |
| 2004/0133247 A1 | 7/2004 | Stahmann et al. |
| 2004/0158289 A1 | 8/2004 | Girouard et al. |
| 2004/0158290 A1 | 8/2004 | Girouard |
| 2004/0161421 A1 | 8/2004 | Komowski et al. |
| 2004/0208845 A1 | 10/2004 | Michal et al. |
| 2004/0213770 A1 | 10/2004 | Seward et al. |
| 2004/0214182 A1 | 10/2004 | Sharma et al. |
| 2004/0215251 A1 | 10/2004 | Sharma et al. |
| 2004/0215253 A1 | 10/2004 | Weinberg |
| 2004/0230274 A1 | 11/2004 | Heil et al. |
| 2004/0253209 A1 | 12/2004 | Soykan et al. |
| 2005/0002912 A1 | 1/2005 | Chachques |
| 2005/0005923 A1 | 1/2005 | Herrin |
| 2005/0008628 A1 | 1/2005 | Feld et al. |
| 2005/0013870 A1 | 1/2005 | Freyman et al. |
| 2005/0021091 A1 | 1/2005 | Laske et al. |
| 2005/0025752 A1 | 2/2005 | Kutryk et al. |
| 2005/0025838 A1 | 2/2005 | Badylak |
| 2005/0043675 A1 | 2/2005 | Pastore et al. |
| 2005/0059153 A1 | 3/2005 | George et al. |
| 2005/0059623 A1 | 3/2005 | Moonen |
| 2005/0059999 A1 | 3/2005 | Mongeon et al. |
| 2005/0096701 A1 | 5/2005 | Donovan et al. |
| 2005/0112759 A1 | 5/2005 | Radisic et al. |
| 2005/0113705 A1 | 5/2005 | Fischell et al. |
| 2005/0118144 A1 | 6/2005 | Zhang |
| 2005/0123526 A1* | 6/2005 | Shafer ............... 424/93.21 |
| 2005/0130136 A1 | 6/2005 | Lee |
| 2005/0137626 A1 | 6/2005 | Pastore et al. |
| 2005/0137631 A1 | 6/2005 | Yu et al. |
| 2005/0137671 A1 | 6/2005 | Liu et al. |
| 2005/0149136 A1 | 7/2005 | Siejko et al. |
| 2005/0192637 A1 | 9/2005 | Girouard et al. |
| 2005/0197674 A1 | 9/2005 | McCabe et al. |
| 2005/0209665 A1 | 9/2005 | Hunter et al. |
| 2005/0209666 A1 | 9/2005 | Hunter et al. |
| 2005/0283197 A1 | 12/2005 | Daum et al. |
| 2005/0288721 A1 | 12/2005 | Girouard et al. |
| 2006/0015146 A1 | 1/2006 | Girouard et al. |
| 2006/0134071 A1 | 6/2006 | Ross et al. |
| 2006/0134079 A1 | 6/2006 | Sih et al. |
| 2006/0136027 A1 | 6/2006 | Westlund et al. |
| 2006/0136028 A1 | 6/2006 | Ross et al. |
| 2006/0148737 A1 | 7/2006 | Harmon |
| 2006/0282123 A1 | 12/2006 | Hunter et al. |
| 2007/0027487 A1* | 2/2007 | Mika et al. ............. 607/9 |
| 2007/0078507 A1 | 4/2007 | Zacouto |
| 2007/0198063 A1 | 8/2007 | Hunter et al. |

FOREIGN PATENT DOCUMENTS

| | | |
|---|---|---|
| EP | 0467695 A2 | 1/1992 |
| EP | 0545628 A2 | 6/1993 |
| EP | 633031 | 1/1995 |
| EP | 1050265 | 11/2000 |
| EP | 1142607 A2 | 10/2001 |
| WO | WO-9208796 | 5/1992 |
| WO | WO-9428143 | 12/1994 |
| WO | WO-9640195 | 12/1996 |
| WO | WO-97/33513 | 9/1997 |
| WO | WO 98/02150 | 1/1998 |
| WO | WO-9802040 A1 | 1/1998 |
| WO | WO-9802150 A1 | 1/1998 |
| WO | WO-9815317 | 4/1998 |
| WO | WO-9815317 A1 | 4/1998 |
| WO | WO-9834537 A1 | 8/1998 |
| WO | WO-9904851 | 2/1999 |
| WO | WO-9925385 A1 | 5/1999 |
| WO | WO-9936563 | 7/1999 |
| WO | WO-0007497 A1 | 2/2000 |
| WO | WO-0017326 | 3/2000 |
| WO | WO-0027466 A1 | 5/2000 |
| WO | WO-0054661 A1 | 9/2000 |
| WO | WO-0062855 A1 | 10/2000 |
| WO | WO-0074584 | 12/2000 |
| WO | WO-0074773 A1 | 12/2000 |
| WO | WO-0103750 | 1/2001 |
| WO | WO-0204063 A1 | 1/2002 |
| WO | WO-0205866 A2 | 1/2002 |
| WO | WO-0249669 A2 | 6/2002 |
| WO | WO-0249714 A2 | 6/2002 |
| WO | WO-02059138 A1 | 8/2002 |
| WO | WO-02070065 A2 | 9/2002 |
| WO | WO-02087681 A2 | 11/2002 |
| WO | WO-01046200 | 2/2004 |
| WO | WO-2004024206 | 3/2004 |
| WO | WO 2004/030706 | 4/2004 |
| WO | WO-2004026394 A1 | 4/2004 |
| WO | WO-2004030706 | 4/2004 |
| WO | WO-2004050180 A2 | 6/2004 |
| WO | WO-2004080533 A1 | 9/2004 |
| WO | WO-2004093969 A1 | 11/2004 |
| WO | WO-2005/046790 | 5/2005 |
| WO | WO-2004080533 A1 | 9/2005 |
| WO | WO-2005084751 A2 | 9/2005 |
| WO | WO-2005084751 A3 | 9/2005 |
| WO | WO-2005120635 A1 | 12/2005 |
| WO | WO-2006019856 A1 | 2/2006 |

OTHER PUBLICATIONS

Allman, Amy J., et al., "Xenogeneic extracellular matrix grafts elicit a TH2-restricted immune response", *Transplantation*, 71(11), (Jun. 15, 2001), 1631-40.

Arnaud, Claire, et al., "iNOS is a medator of the heat stress-induced preconditioning against myocardial infarction in vivo in the rat", *Cardiovascular Research*, 58, (2003), 118-125.

Askari, Arman T., et al., "Targeted Gene Therapy for the Treatment of Cardiace Dysfunction", *Seminars in Thoracic and Cardiovascular Surgery*, 14(2), (Apr. 2002), 167-177.

Badylak, Stephen, et al., "Extracellular Matrix for Myocardial Repair"*Heart Surgery Forum*, 6(2), (2003), E20-E26.

Badylak, Stephen F., et al., "Marrow-Derived Cells Populate Scaffolds Composed of Xenogeneic Extracellular Matrix", *Experimental Hematology*, 29(11), (Nov. 2001), 1310-8.

Badylak, Stephen F., et al., "Resorbably bioscaffold for esophageal repair in a dog model", *Journal of Pediatric Surgery*, 35(7), (Jul. 2000), 1097-1103.

Badylak, Stephen F., "The Extracellular Matrix as a Scaffold for Tissue Reconstruction", *Seminars in Cell Developmental Biology*, 13(5), (Oct. 2002), 377-83.

Baker, A. H., "Development and Use of Gene Transfer for Treatment of Cardiovascular Disease", *J Card Surg*, 17, (2002), 543-548.

Barbone, Alessandro, et al., "Comparison of right and left ventricular responses to left ventricular assist device support in patients with severe heart failure: a primary role of mechanical unloading underlying reverse remodeling", *Circulation*, 104(6), (Aug. 7, 2001), 670-675.

Boheler, Kenneth R., et al., "Differentiation of Pluripotent Embryonic Stem Cells into Cardiomyocytes", *Circulation Research*, 91(3), (Aug. 9, 2002), 189-201.

Bralet, J, et al., "Vasopeptidase inhibitors: an emerging class of cardiovascular drugs", *Trends Pharmacol Sci.*, 22(3), (Mar. 2001), 106-9.

Brugada, R., et al., "Genetics of Cardiovascular Disease with Emphasis on Atrial Fibrillation", *Journal of Interventional Cardiac Electrophysioilogy*, 3, (1999),7-13.

Brundel, B. J., et al., "Alterations in Potassium Channel Gene Expression in Atria of Patients With Persistent and Paroxysmal Atrial Fibrillation: Differential Regulation of Protein and mRNA Levels for K+ Channels", *Journal of the American College of Cardiology*, 37(3), (2001), 926-932.

Brunner, Friedrich, "Attenuation of myocardial ischemia/reperfusion injury in mice with myocyte-specific overexpression of endothelial nitric oxide synthase", *Cardiovascular Research*, 57, (2003), 55-62.

Burton, D. Y., et al., "The Incorporation of an Ion Channel Gene Mutation Associated with the Long QT Syndrome (Q9E-hMiRPI) in a Plasmid Vector for Site-Specific Arrhythmia Gene Therapy: In Vitro and In Vivo Feasibility Studies", *Human Gene Therapy*, 14, (2003), 907-922.

Cheng, C.-F., et al., "Genetic Modifiers of Cardiac Arrhythmias", *Trends in Molecular Medicine*, 9(2), (2003), 59-66.

Cleland, J. G., et al., "Update of Clinical Trials from the American College of Cardiology 2003. Ephesus, Sportif-III*, Ascot, Companion, UK-PACE and T-wave Alternans", *The European Journal of Heart Failure*, 5, (2003), 391-398.

Colonna, P., "Infarction and left ventricular remodeling: results of the CEDIM trial. Carnitine Ecocardiografia Digitalizzata Infarto Miocardico.", *Am Heart J.*, (Feb. 2000), 139(2 Pt 3)), S124-30.

Condorelli, G., et al., "Cardiomyocytes Induce Endothelial Cells to Trans-Differentiate into Cardiac Muscle: Implications for Myocardium Regeneration", *PNAS*, 98(19), (Sep. 11, 2001), 10733-10738.

Daum, Douglas R., "Systems and Methods for Hypotension", U.S. Appl. No. 11/141,260, filed May 31, 2005, 51 pages.

Del Monte, F., et al., "Targeting Calcium Cycling Proteins in Heart Failure Through Gene Transfer", *The Journal of Physiology*, 546(1), (2002), 49-61.

Depre, Christophe, et al., "Metabolic Aspects of Programmed Cell Survival and Cell Death in The Heart", *Cardiovascular Research*, 45(3), (Feb. 2000), 538-548.

Dobrev, D., et al., "Molecular Basis of Downregulation of G-Protein-Coupled Inward Rectifying K+ Current (I k,aCh) in Chronic Human Atrial Fibrillation", *Circulation*, 104, (2001), 2551-2557.

Donahue, J. K., et al., "Focal Modification of Electrical Conduction in the Heart by Viral Gene Transfer", *Nature Medicine*, 6(12), (2000), 1395-1398.

Ferdinandy, Peter, et al., "Nitric oxide, superoxide, and peroxynitrite in myocardial ischemia-reperfusion injury and preconditioning", *British Journal of Pharmacology*, 138(4), (2003), 532-543.

Flogel, Ulrich, "Myoglobin: A scanvenger of bioactive NO", *PNAS*, 98(2), (Jan. 16, 2001),735-740.

Freedman, Saul B., et al., "Therapeutic Angiogenesis for Ischemic Cardiovascular Disease", *J. Mol Cell Cardiol.*, 33(3), (Mar. 2001),379-393.

Gabouev, A I., et al., "In Vitro Construction of Urinary Bladder Wall Using Porcine Primary Cells Reseeded on Acellularized Bladder Matrix and Small Intestinal Submucosa", *The International Journal of Artificial Organs*, 26(10), (Oct. 2003), 935-42.

Gewaltig, Michael T., "Vasoprotection by nitric oxide: mechanisms and therapeutic potential", *Cardiovascular Research*, 55, (Feb. 14, 2005), 250-260.

Girouard, Steven D., et al., "Method and Apparatus for Controlled Gene or Protein Delivery", U.S. Appl. No. 10/890,825, filed Jul. 14, 2004, 61 Pgs.

Girouard, S. d., "Methods and Apparatus to Modulate Cellular Regeneration Post Myocardial Infarct", U.S. Appl. No. 10/862,716, filed Jun. 7, 2004, 71 Pages.

Gould, P. A., et al., "Review of the Current Management of Atrial Fibrillation", *Expert Opinion on Pharmacotherapy*, 4(11), (2003), 1889-1899.

Graham, Regina M., et al., "Gene and Cell Therapy for Heart Disease", *IUBMB Life*, 54, (2002), 59-66.

Hakuno, Daihiko, et al., "Bone Marrow-Derived Regenerated Cardiomyocytes (CMG Cells) Express Functional Adrenergic and Muscarinic Receptors", *Circulation*, 105, (Jan. 22, 2002), 380-386.

Hamawy, A. H., et al., "Cardiac Angiogenesis and Gene Therapy: A Strategy for Myocardial Revascularization", *Current Opinion in Cardiology*, 14, (1999), 515-522.

Harjai, Kishore J., et al., "Therapeutic Angiogenesis: a Fantastic New Adventure", *Journal of Interventional Cardiology*, 15(3), (2002), 223-229.

Heerdt, Paul M., et al., "Chronic Unloading By Left Ventricular Assist Device Reverses Contractile Dysfunction and Alters Gene Expression in End-Stage Heart Failure", *Circulation*, 102(22), (Nov. 28, 2000), 2713-2719.

Laham, Roger J., et al., "Gene Transfer to Induce Angiogenesis in Myocardial and Limb Ischaemia", *Expert Opin Biol Ther.*, 1(6),, (2001), pp. 985-994.

Lee, L. Y., et al., "Exogenous Control of Cardiac Gene Therapy: Evidence of Regulated Myocardial Transgene Expression After Adenovirus and Adeno-Associated Virus Transfer of Expression Cassettes Containing Corticosteroid Response Element Promoters", *J Thorac Cardiovasc Surg*, 118, (1999), 26-35.

Lehman, J., et al., "Gene regulatory mechanisms governing energy metabolism during cardiac hypertrophic growth", *Heart Fail Rev.*, (Apr. 2000), 175-85.

Levin, L., "Researchers present findings at European cardiology conference", *Advisory Board Daily Briefing, 8. Clinical Outlook*, (Sep. 2002),8 pages [see pp. 5,6].

Li, Qianghong, "Gene Therapy With Inducible Nitric Oxide Synthase Protects Against Myocardial Infarction via a Cyclooxygenase-2-Dependent Mechanism", *Circulation Research*, 92, (2003), 741-748.

Lin, H., "Specific Region of the c-myc Promoter is Responsive to Electric and Magnetic Fields", *Journal of Cellular Biochemistry*, 54, (1994),281-288.

Lin, H., "Regulating Genes with Electromagnetic Response Elements", *Journal of Cellular Biochemistry*, 81, (2001), 143-148.

Lodie, Tracey A., et al., "Systematic Analysis of Reportedly Distinct Populations of Multipotent Bone Marrow-Derived Stem Cells Reveals a Lack of Distinction", *Tissue Engineering*, vol. 8, No. 5,, (2002), pp. 739-751.

Lopaschuk, G., "Metabolic abnormalities in a diabetic heart", *Heart Fail Rev.*, (Apr. 2002), 149-59.

Losordo, Douglas W., et al., "Gene Therapy for Myocardial Angiogenesis", *Am Heart J.*, vol. 138,, (1999), pp. S132-S141.

Lovett, Eric G., "Technique for Discriminating Between Coordinated and Uncoordinated Cardiac Rhythms", U.S. Appl. No. 10/435,487, filed May 9, 2003, assigned to Cardiac Pacemakers, Inc., (May 9, 2003), 36 pgs.

Luttun, A., et al., "The Role of Proteinases in Angiogenesis, Heart Development, Restenosis, Atherosclerosis, Myocardial Ischemia, and Stroke: Insights from Genetic Studies", *Current Athersclerosis Reports*, 2, (2000), 407-416.

MacNeill, MD, B. D. et al., "Targeting Signaling Pathways in Heart Failure by Gene Transfer", *Current Atherosclerosis Reports*, 5, (2003), 178-185.

Mann, Brenda K., et al., "Tissue Engineering in the Cardiovascular System: Progress Toward a Tissue Engineered Heart", *Anat Rec.* 263,, (2001), pp. 367-371.

Marban, E., et al., "Gene Therapy for Cardiac Arrhythmias", *Cold Spring Harbor 4 Symposia in Quantitative Biology*, vol. LXVII—The Cardiovascular System, Published by Cold Spring Harbor Laboratory Press, (2002), 527-531.

Mbai, M., et al., "Genetic Basis for the Origin of Cardiac Arrhythmias: Implications for Therapy", *Current Cardiology Reports*, 4, (2002), 411-417.

McPherson, T.B., et al., "Galalpha(1,3)Gal epitope in porcine small intestinal submucosa", *Tissue Engineering*, 6(3), (Jun. 2000), 133-9.

Meezan, Elias, et al., "A simple, versatile, nondisruptive method for the isolation of morphologically and chemicaly pure basement membranes from several tissues", *Life Sciences*, 17(11), (Dec. 1, 1974), 1721-32.

Menasche, Philippe, "Cell Theraph of Heart Failure", *CR Biologies*, vol. 325,, (2002),pgs. 731-738.

Michal, Eugene T., et al., "Methods and Compositions to Treat Myocardiac Conditions", U.S. Appl. No. 10/802,955, filed Mar. 16, 2004, 113 pgs.

Miller, L. W., et al., "Limitations of Current Medical Therapies for the Treatment of Heart Failure", *Reviews in Cardiovascular Medicine*, 4(Suppl. 2), (2003),S21-S29.

Min, Mart, et al., "Electrical Impedance and Cardiac Monitoring-Technology, Potential and Applications", *International Journal of Bioelectromagnetism*, vol. 5, No. 1, (2003), 53-56.

Miyagawa, Shigeru, et al., "Myocardial Regeneration Therapy for Heart Failure: Hepatocyte Growth Factor Enhances The Effect of Cellular Cardiomyoplasty", *Circulation*, 105(21), (May 28, 2002), 2556-2561.

Nemer, Georges, et al., "Regulation of Heart Development and Function Through Combinatorial Interactions of Transcription Factors", *The Finnish Medical Society Duodecim, Ann Med*, vol. 33,, (2001), pp. 604-610.

Nuss, H. B., et al., "Reversal of Potassium Channel Deficiency in Cells from Failing Hearts by Adenoviral Gene Transfer: A Prototype for Gene Therapy for Disorders of Cardiace Excitability and Contractility", *Gene Therapy*, 3, (1996), 900-912.

Orlic, Donald, et al., "Bone Marrow Cells Regenerate Infarcted Myocardium", *Nature*, vol. 410,, (Apr. 5, 2001), pp. 701-705.

Ostadal, Petr, et al., "The effect of early treatment by cerivastatin on the serum level of C-reactive protein, interleukin-6, and interleukin-8 in patients with unstable angina and non-Q-wave myocardial infarction", *Molecular and Cellular Biochemistry*, 246, (2003), 45-50.

Paolocci, Nazareno, et al., "Positive inotropic and lusitropic effects of HNO/NO-in failing hearts: Independence from beta-adrenergic signaling", *Proceedings of the National Academy of Sciences USA*, 100(9), (Apr. 29, 2003), 5537-5542.

Paolocci, N azareno, "Positive inotropic and lusitropic effects of HNO/NO- in failing hearts: independence from beta1-adrenergic signaling", *Proceedings of the National Academy of Sciences USA*, 100(9), (Apr. 29, 2003), 4978-80.

Pastore, Joseph M., et al., "Method and Apparatus for Device Controlled Gene Expression for Cardiac Protection", U.S. Appl. No. 11/220,397, filed Sep. 6, 2005, 68 Pgs.

Pasumarthi, Kishore B., et al., "Cardiomyocyte Cell Cycle Regulation", *Circ Res.*, vol. 90,, (2002), pp. 1044-1054.

Patberg, Kornelis W., et al., "Cardiac Memory Is Associated With Decreased Levels of the Transcriptional Factor CREB Modulated by Angiotensin II and Calcium", *Circulation Research*, vol. 93, (2003), 472-478.

Pimentel, Rhae C., et al., "Autocrine Regulation of Myocyte Cx43 Expression by VEGF", *Circ Res.*, 90:, (2002), pp. 671-677.

Pouzet, Bruno, et al., "Intramyocardial transplantation of Autologous Myoblasts: Can Tissue Processing Be Optimized?", *Circulation*, vol. 102,, (2000), pp. III-210III-215.

Prinzen, Frits W., et al., "Mapping of Regional Myocardial Strain and Work During Ventricular Pacing: Experimental Study Using Magnetic Resonance Imaging Tagging", *Journal of American College of Cardiology*, vol. 33, No. 6,, (1999),pp. 1735-1742.

Radisic, M., "From the Cover: Functional assembly of engineered myocardium by electrical stimulation of cardiac myocytes cultured on scaffolds", *Proc Natl Acad Sci U S A.*, 101(52), (Dec. 28, 2004), 18129-34.

Reinecke, Hans, et al., "Survival, Integration, and Differentiation of Cardiomyocyte Grafts: a Study in Normal and Injured Rat Hearts", *Circulation,*, (1999), pp. 193-202.

Rizos, I., "Three-year survival of patients with heart failure caused by dilated cardiomyopathy and L-carnitine administration", *Am Heart J.*, 139(2 Pt 3), (Feb. 2000), Am Heart J.

Robbins, Jeffrey, "Remodeling the Cardiac Sarcomere Using Transgenesis", *Annu Rev Physiol.*, vol. 62,, (2000), pp. 261-287.

Roberts, R., et al., "Genetic Aspects of Arrhythmias", *American Journal of Medical Genetics (Semin. Med. Genet.)*, 97, (2000), 310-318.

Ross, Jeffrey, "Epicardial Patch Including Isolated Extracellular Matrix With Pacing Electrodes", U.S. Appl. No. 11/017,627, filed Dec. 20, 2004, 87 pgs.

Ross, Jeffrey, et al., "Use of Extracellular Matrix and Electrical Therapy", U.S. Appl. No. 11/017,237, filed Dec. 20, 2004, 89 pgs.

Rubenstrunk, A., "Transcriptional Activation of Metallothionein I Gene by Electric Pulses in vivo: Basis for the Development of a New Gene Switch System", *The Journal of Gene Medicine*, 5, (2003), 773-783.

Rutanen, J., et al., "Progress and Prospects—Post-Interventiona Vessel Remodeling", *Gene Therapy*, 9, (2002),1487-1491.

Sabbah, H., et al., "Partial fatty acid oxidation inhibitors: a potentially new class of drugs for heart failure", *Eur J Heart Fail.*, 4(1), (Jan. 2002),3-6.

Salloum, Fadi, "Sildenafil Induces Delayed Preconditioning Through Inducible Nitric Oxide Synthase-Dependent Pathway in Mouse Heart", *Circulation Research*, 92, (Apr. 4, 2003), 595-597.

Sarikaya, Ayda, et al., "Antimicrobial Activity Associated With Extracellular Matrices", *Tissue Engineering*, 8(1), (Feb. 2002), 63-71.

Schram, G., et al., "Differential Distribution of Cardiac Ion Channel Expression as a Basis for Regional Specialization in Electrical Function", *Circulation Research*, 90, (2002), 939-950.

Shimizu, Tatsuya, et al., "Cell Sheet Engineering for Myocardial Tissue Reconstruction", *Biomaterials*, 24(13), (Jun. 2003), 2309-2316.

Shin, Heungsoo , et al., "Biomimetic materials for tissue engineering", *Biomaterials*, 24(24), (Nov. 2003), 4353-64.

Sih, Harris J., "Implantable Medical Devices Comprising Isolated Extracellular Matrix", U.S. Appl. No. 11/017,432, filed Dec. 20, 2004, 87 pgs.

Stanley, W., et al., "Energy metabolism in the normal and failing heart: potential for therapeutic interventions", *Heart Fail Rev.*, (Apr. 2002),115-30.

Stanley, W., "Partial fatty acid oxidation inhibitors for stable angina", *Expert Opin Investig Drugs*, 11(5), (May 2002), 615-29.

Stock, Ulrich A., et al., "Tissue Engineering: Current State and Prospects", *Annu. Rev Med.*, 52, (2001), 443-51.

Suematsu, Yoshihiro , et al., "L-Arginine given after ischaemic preconditioning can enhance cardioprotection in isolated rat hearts", *European Journal of Cardio-thoracic Surgery*, 19, (2001), 873-879.

Suzuki, Ken, et al., "Cell transplantation for the Treatment of Acute Myocardial Infarction Using Vascular Endothelial Growth Factor-Expressing Skeletal Myoblasts", *Circulation*; 104[suppl 1],, (2001), pp. I207-I212.

Taylor, Doris A., et al., "Regenerating Functional Myocardium: Improved Performance after Skeletal Myoblast Transplantation", *Nature Medicine*, vol. 4, No. 8,, (Aug. 1998), pp. 929-933.

Terracio, Louis, et al., "Effects of Cyclic Mechanical Stimulation of the Cellular Components of the Heart: In Vitro.", *In Vitro Cellular & Develomental Biology*, vol. 24, No. 1,, (Jan. 1988), pp. 53-58.

Thijssen, V. J., et al., "Analysis of Altered Gene Expression During Sustained Atrial Fibrillation", *Cardiovascular Research*, 54, (2002), 427-437.

Tomaselli, F., et al., "Photodybnamic Therapy Enhanced by Hyperbaric Oxygen in Acute Endoluminal Palliation of Malignant Bronchial Stenosis (Clinical Pilot Study in 40 Patients)", *European Journal of Cardio-thoracic Surgery*, 19, (2001), 549-554.

Towbin, J. A., et al., "Chapter 3—Genetics and Cardiac Arrhythmias", *In Advances in Pediatrics*, vol. 29, Published by Mosby, Inc.,(2002), 87-129.

Tran, Nguyen, et al., "Autologous Cell Transplantation and Cardiac Tissue Engineering: Potential Applications in Heart Failure", *Biorheology*, 40(1-3), (2003), 411-15.

Van Gelder, MD, I. C., et al., "Alterations in Gene Expression of Proteins Involved in the Calcium Handling in Patients with Atrial Fibrillation", *J Cardiovasc Electrophysical*, 10, (1999), 552-560.

Walther, W., et al., "Cell Type Specific and Inducible Promoters for Vectors in Gene Therapy as an Approach for Cell Targeting", *Journal of Molecular Medicine*, 74, (1996),379-392.

Washizu, Masao, et al., "Handling Biological Cells Using a Fluid Integrated Circuit", *IEEE Transactions on Industry Application*, vol. 26, No. 2, (Mar./Apr. 1990), 352-358.

Wattanapitayakul, S. K., et al., "Recent Developments in Gene Therapy for Cardiac Disease", *Biomedical & Pharmacotherapy*, 54, (2000), 487-504.

Westlund, Randy, "Lead Electrode Incorporating Extracellular Matrix", U.S. Appl. No. 11/017,238, filed Dec. 20, 2004, 85 pgs.

Wobus, Anna M., et al., "Embryonic Stem CellDerived Cardiac Differnetiation: Modulation of Differentiation and "Loss-of_Function" Analysis In Vitro", *TCM*. vol. 8, No. 2,, (1998), pp. 64-74.

Woldbaek, Per R., et al., "Increased cardiac IL-18 mRNA, pro-IL-18 and plasma IL-18 after myocardial infarction in the mouse; a potential role in cardiac dysfunction", *Cardiovascular Research*, 59, (2003), 122-131.

Wolff, A., et al., "Metabolic approaches to the treatment of ischemic heart disease: the clinicians' perspective", *Heart Fail Rev.*, (Apr. 2002), 187-203.

Wolfrum, Sebastian, et al., "Acute Reduction of Myocardial Infarct Size By a Hydroxymethyl Glutaryl Coenzyme A Reductase Inhibitor Is Mediated By Endothelial Nitric Oxide Synthase", *J. Cardiovas Pharamcol*, vol. 41, No. 3, (Mar. 2003), 474-480.

Wuderlich, Carsten, "Acute Inhibition of Myoglobin Impairs Contractility and Energy State of iNOS-Overexpressing Hearts", *Circulation Research*, 92, (2003), 1352-1358.

Wyman, T., et al., "Promoter-Activated Expression of Nerve Growth Factor for Treatment of Neurodegenerative Diseases", *Gene Therapy*, 6, (1999),1648-1660.

Wynn, R., "Cardiovascular drugs and dental considerations", *Cardiovascular drugs and dental considerations. J Calif Dent Assoc.*, 28(7), (Jul. 2000), 9-26.

Xu, Chunhui, et al., "Characterization and Enrichment of Cardiomyocytes Derived from Human Embryonic Stem Cells", *Circ Res.*, vol. 91,, (2002), pp. 501-508.

Zhu, Fangyi, et al., "Purification, characterization and Evaluation of Antibacterial Peptide from Resorbable Tissue Scaffold", *Abstracts of Papers American Chemical Society*, 224(1-2), (Abstract No. BIOT 137), (2002).

Zhuang, Jianping, et al., "Pulsatile Stretch Remodels Cell-to-Cell Communication in Cultured Myocytes", *Circ Res.*, 87,, (2000), pp. 316-322.

Zimmermann, WH, et al., "Tissue Engineering of a Differentiated Cardiac Muscle Construct", *Circ Res.*, vol. 90,, (2002), pp. 223-230.

Buchwald, A B., et al., "Decoy Oligodeoxynucleotide Against Activator Protein-1 Reduces Neointimal Proliferation After Coronary Angioplasty in Hypercholesterolemic Minipigs", *Journal of the American College of Cardiology*, 39(4), (Feb. 20, 2002),732-738.

Zou, Y. , et al., "Heat Shock Transcription Factor 1 Protects Cardiomyocytes From Ischemia/Reperfusion Injury", *Circulation*, 108 (24) ISSN: 1524-4539 XP002345863, (Dec. 16, 2003),3024-3030.

"International Search Report for Application No. PCT/US2005/006069, date mailed Oct. 20, 2005", 19 Pages.

Avitall, B., "Iontophoretic transmyocardial drug delivery. A novel approach to antiarrhythmic drug therapy.", *Circulation*, 85(4), (Apr. 1992), 1582-93.

Bovenberg, W. A., et al., "Expression of recombinant human insulin-like growth factor I in mammalian cells", *Mol Cell Endocrinol.*, 74(1), (Nov. 12, 1990), 45-59.

Frey, Norbert, "Decoding calcium singals involved in cardiac growth and function", *Nature Medicine* 6(11), (2000), 1221-1227.

Gunatillake, Pathiraja A., et al., "Biodegradable Synthetic Polymers for Tissue Engineering", *European Cells and Materials 5*, (2003), 1-16.

Kanikkannan, Narayanasamy, "Iontophoresis-Based Transdermal Delivery Systems", *Biodrugs* 16(5), (2002), 339-347.

MacGowan, G. A., et al., "New molecular insights into heart failure and cardiomyopathy: potential strategies and therapies", *Ir J Med Sci.*, 171(2), (Apr.-Jun. 2002), 99-104.

Oudit, Gavin Y., et al., "The Molecular Physiology of the Cardiac Transient Outward Potassium Current (Ito) in Normal and Diseased Myocardium", *I Mol Cell Cardiol 33*, (2001), 851-872.

Recer, P., "Researches find first heart attack gene", *AP Science News, Science*: www.science.org, (2003).

Wurm, F. M., et al., "Inducible overproduction of the mouse c-myc protein in mammalian cells", *Proct Natl Acad Sci U S A.*, 83(15), (Aug. 1986), 5414-8.

"COOK SIS Technology: Scientific Information: Clinical References", http://www.cooksis.com/sci/ref1.html, (2004), 4 pgs.

"COOK SIS Technology: Scientific Information: Safety", http://www.cooksis.com/sci/tech3.html, (2004), 2 pgs.

"COOK SIS Technology: Scientification Information: Tissue Repair: Challenges & Complications", http://www.cooksis.com/sci/tech.html, (2004), 2 pgs.

Akiyama-Uchida, Y., et al., "Norepinephrine enhances fibrosis mdiated by TGF-beta in cardiac fibroblasts", *Hypertension*, 40(2), (Aug. 2002),148-54.

Aukrust, Pal, et al., "Immunomodulating Therapy: New Treatment Modality in Congestive Heart Failure", *Congest Heart Fail.*, 9(2), (Mar.-Apr. 2003), 64-69.

Bader, A., et al., "Tissue engineering of heart valves Å? human endothelial cell seeding of detergent acellularized procine valves", *Eur J Cardiothorac Surg*, 14(3), (Sep. 1998), 279-84.

Bell, E., *Tissue Engineering: Current Perspectives*, Burkhauser Publishers, Cambridge, MA,(1993), 179-189.

Bigatel, D. A., et al., "The matrix metalloproteinase inhibitor BB-94 limits expansion of experimental abdominal aortic aneurysms", *J Vasc Surg*, 29(1), (1999), 130-8.

Capecchi, M. R., "High efficiency transformation by direct microinjection of DNA into cultured mammalian cells.", *Cell*, 22(2 Pt 2), (Nov. 1980), 479-88.

Chu, G., "SV40 DNA transfection of cells in suspension: analysis of efficiency of transcription and translation of T-antigen.", *Gene*, 13(2), (Mar. 1981), 197-202.

Colucci, Wilson S., "Molecular and Cellular Mechanisms of Myocardial Failure", *Am J Cardiol* 80(11A), (1997), 15L-25L.

Courtman, D. W., et al., "Development of a pericardial acellular matrix biomaterial: Biochemical and mechanical effects of cell extraction", *J Biomed Materi Res.*, 28(6), (1994), 655-66.

Cserjesi, P., "Myogenin induces the myocyte-specific enhancer binding factor MEF-2 independently of other muscle-specific gene products", *Mol Cell Biol*, 11(10), (Oct. 1991), 4854-62.

Curiel, D. T., et al., "Adenovirus enhancement of transferrin-polylysine-mediated gene delivery", *Proc. Natl Acad Sci USA.*, 88(19), (Oct. 1, 1991), 8850-4.

Curtil, A., et al., "Freeze Drying of Cardiac Valves in Preparation for Cellular Repopulation", *Cryobiology*, 34(1), (Feb. 1997), 13-22.

Dhawan, J., "Tetracycline-regulated gene expression following direct gene transfer into mouse skeletal muscle", *Somat Cell Mol Genet.*, 21(4), (1995), 233-40.

Eckardt, Lars, et al., "Load-induced changes in repolarization: evidence from experimental and clinical data", *Basic Res Cardiol*, 96(4), (2001), 369-380.

Felgner, P., L., "Lipofection: A highly efficient, lipid-mediated DNA-transfection procedure", *Proceedings of the National Academy of Sciences*, 84, Biochemistry,(Nov. 1987), pp. 7413-7417.

Graham, F. L., "A New Technique for the Assay of Infectivity of Human Adenovirus 5 DNA", *Virology*, 52, (1973), 456-467.

Hafizi, S., et al., "Inhibition of human cardiac fibroblast mitogenesis by blockade of mitogen-activated protein kinase and phosphatidylinositol 3-kinase.", *Cir Exp Pharma Physiol*, 26(7), (Jul. 1999), 511-3.

Hammond, H. K., et al., "Regional myocardial downregulation of the inhibitory guanosine triphosphate-binding protein (Gi alpha 2) and beta-adrenergic receptors in a porcine model of chronic episodic myocardial ischemia", *J Clin Res*, 92(6), (1993),2644-52.

Higashi, T., et al., "Pharmacological characterization of endothelin-induced rat pulmonary arterial dilatation", *Br J Pharmacol*, 121(4), (1997), 782-6.

Johnson, J. E., "Muscle creatine kinase sequence elements regulating skeletal and cardiac muscle expression in transgenic mice", *Mol Cell Biol.*, 9(8), (1989), 3393-9.

Jugdutt, Bodh I., "Remodeling of the Myocardium and Potential Targets in the Collagen Degradation and Synthesis Pathways", *Current Drug Targets Cardiovascular & Haematological Disorders*, 3, (2003), 1-30.

Kiba, A., et al., "VEGFR-2-specific ligand VEGF-E induces non-edematous hyper-vascularization in mice.", *Biochem Biophys Res Commun.*, 301(2), (Feb. 7, 2003), 371-7.

Klein, T.M., "High-Velocity Microprojectiles for Delivering Nucleic Acids into Living Cells", *Nature*, 327, (1987), 70-73.

Kodama, I., et al., "Cellular electropharmacology of amiodarone.", *Cardiovas Res*, 35(1), (1997), 13-29.

Lijnen, P. J., et al., "Induction of Cardiac Fibrosis by Transforming Growth Factor-B1", *Molecular Genetics and Metabolism*, 71, (2000), 418-435.

Mackenna, Deidre, et al., "Role of mechanical factors in modulating cardia fibroblast function and extracellular matrix synthesis", *Cardiovascular Research*, 46, (2000), 257-263.

Mader, S., "A steroid-inducible promoter for the controlld overexpression of cloned genes in eukaryotic cells", *Proc Natl Acad Sci USA*, 90(12), (1993), 5603-7.

Mannino, R. J., "Liposome mediated gene transfer.", *BioTechniques*, 6(7), (Jul.-Aug. 1988), 682-90.

Muscat, G. E., "Multiple 5'-flanking regions of the human alpha-skeletal actin gene synergistically modulate muscle-specific expression", *Mol Cell Biol*, 7(11), (1987), 4089-99.

Palermo, J., "Transgenic remodeling of the contractile apparatus in the mammalian heart", *Circ Res*, 78(3), (1996), 504-9.

Pouleur, H., et al., "Changes in plasma renin activity and haemodynamics during vasodilator therapy in conscious dogs with myocardial infarction or chronic volume overload.", *Eur J Clin Investig*, 13(4), (1983), 331-8.

Pouzet, B., "Intramyocardial transplantation of autologous myoblasts: can tissue processing be optimized?", *Circulation*, 102(19 Suppl 3), (2000), III210-5.

Rinsch, C., et al., "Delivery of FGF-2 but not VEGF by encapsulated genetically engineered myoblasts improves survival and vascularization in a model of acute skin flap ischemia", *Gene Therapy*, 8, (2001), 523-533.

Roth, D. A., et al., "Downregulation of cardiac guanosine 5'-triphosphate-binding proteins in right atrium and left ventricle in pacing-induced congestive heart failure", *J Clin Invest.*, 91(3), (Mar. 1993), 939-49.

Sam, Flora, et al., "Role of Endothelin-1 in Myocardial Failure", *Proceedings of the Association of American Physicians*, 111(5), (1999), 417-422.

Semenza, G. L., "Hypoxia-inducible nuclear factors bind to an ehancer element located 3' to the human erythropoietin gen", *Proc Natl Acad Sci USA*, 88(13), (1991), 5680-4.

Semenza, G. L., "Transcriptional regulation of genes encoding glycolytic enzymes by hypoxia-inducible factor 1", *J Biol Chem*, 269(38), (1994), 23757-63.

Shigekawa, K., "Electroproation of Eukaryotes and Prokaryotes: A General Approach to the Introduction of Macromolecules into Cells", *BioTechniques*, 6, (1988), 742-751.

Shockett, P., "A modified tetracycline-regulated system provides autoregulatory, inducible gene expression in cultured cells and transgenic mice", *Proc Natl Acad Sci USA*, 92(14), (1995), 6522-6.

Sukenaga, Y., et al., "Development of the chymase inhibitor as an anti-tissue-remodeling drug: myocardial infarction and some other possibilities", *Jap J Pharmacol*, 90(3), (2002), 218-22.

Taylor, D. A., et al., "Delivery of primary autologous skeletal myoblasts into rabbit heart by coronary infusion: a potential approach to myocardial repair", *Proc Assoc Am Phys*, 109(3), (May 1997), 245-53.

Villarreal, F. J., et al., "Human cardiac fibroblasts and receptors for angiotensin II and bradykinin: A potential role for bradykinin in the modulation of cardiac extracellular matrix", *Basic research in cardiology*, 93 Supp 3, (1998), s004-s007.

Walter, Dirk H., et al., "Endothelial progenitor cells: regulation and contribution to adult neovascularization", *Herz*, 27(7), (2002), 579-588.

Wang, G. L., et al., "Molecular basis of hypoxia-induced erythropoietin expression", *Curr Opin Hematol.*, 3(2), (Mar. 1996), 156-62.

Wang, L., "Mutation of MEF2A in an inherited disorder with features of coronary artery disea", *Science*, 302(5650), (Nov. 28, 2003), 1578-81.

Weintraub, H., "The myoD gene family: nodal point during specification of the muscle cell lineage", *Science*, 251(4995), (Feb. 15, 1991), 761-6.

Yagi, A., et al., "Anti-inflammatory constitutents, aloesin and aloemannan in Aloe species and effects of tanshinon VI in Salvia miltiorrhiza on heart", *J Pharm Soc Japan*, 123(7), (Jul. 2003), 517-32.

Zimmermann, W. H., et al., "Tissue engineering of a differentiated cardiac muscle construct", *Circulation Res.*, 90(2), (2002), 223-30.

Hodde, Jason P., et al., "Retention of Endothelial Cell Adherence to Porcine-Derived Extracellular Matrix After Disinfection and Sterilzation", *Tissue Engineering*, 8(2), (Apr. 2002), 225-34.

Hong, Y. S., et al., "Localized Immunosuppression in the Cardia Allograft Induced by a New Liposome-Mediated IL-10 Gene Therapy", *J. Heart Lung Transplant*, 21, (2002), 1188-1200.

Huq, F. , et al., "Session 5: Cellular and Subcellular Basis of Remodeling—Modulating Signalling Pathways in Hypertrophy and Heart Failure by Gene Transfer", *Journal of Cardiac Failure*, 8(6)(Suppl.), (2002), S389-S400.

Ingber, Donald E., "Mechanical signaling and the cellular response to extracellular matrix in angiogenesis and cardiovascular physiology", *Circulation Research*, 91(10), (Nov. 15, 2002), 877-87.

Isner, Jeffrey M., "Myocardial Gene Therapy", *Nature*, vol. 415,, (Jan. 10, 2002).

Jackson, KathyJo A., et al., "Regeneration of Ischemic Cardiac Muscle and Vascular Endothelium By Adult Stem Cells", *The Journal of Clinical Investigation*, vol. 107, No. 11,, (Jun. 2001), 1395-1402 pgs.

Jain, Mohit, et al., "Cell therapy attenuates deleterious ventricular remodeling and improves cardiac performance after myocardial infarction", *Circulation*, 103(14), (Apr. 10, 2001), 1920-1927.

Jayakumar, MD, J., et al., "Gene Therapy for Myocardial Prevention—Transfection of Donor Hearts With Heat Shock Protein 70 Gene Protects Cardiac Function Against Ischemia-Reperfusion Therapy", *Circulation*, 102 (Suppl. III), (2000), III-302-III-306.

Kehat, Izhak, et al., "Human Embryonic stem Cells Can Differentiate into Myocytes with Structural and Functional Properties of Cardiomyocytes", *The Journal of Clinical Investigation*, vol. 108, No. 3,, (Aug. 2001), pp. 363-364.

Koch, W. J., et al., "Gene Transfer of B-Adrenergic Signalling Components for Heart Failure", *Journal of Cardiac Failure*, 8(6) (Suppl.), (2002), S526-S531.

Kocher, A.A., et al., "Neovascularization of Ischemic Myocardium by Human Bone-Marrow-Derived Angioblasts Prevents Cardiomyocte Apoptosis, Reduces Remodeling and Improves Cardiac Function", *Nature Medicine*, vol. 7, No. 4,, (Apr. 2001), pp. 430-436.

Komuro, Issei, et al., "Control of Cardiac Gene Expression by Mechanical Stress", *Annu Rev Physiol.*,, (1993), pp. 55-75.

Kozarsky, K. F., "Gene Therapy for Cardiovascular Disease", *Current Opinion in Pharmacology*, 1, (2001), 197-202.

Krum, Henry "New and Emerging Pharmacological Strategies in the Management of Chronic Heart Failure", *Current Opinion in Pharmacology*, 1(2), (Apr. 2001), 126-33.

Cate, F. U., et al., "Endocardial and epicardial steroid lead pacing the neonatal and paediatric age group", *Heart*, 88(4), (2002),392-396.

Cohen, Mitchell I., et al., "Permanent epicardial pacing in pediatric patients: seventeen years of experience and 1200 outpatient visits.", *Circulation*, 103(21), (2001),2585-2590.

Conley, B. J., et al., "Derivation, propagation and differentiation of human embryonic stem cells", *The International Journal of Biochemistry & Cell Biology*, 36, (2004),555-567.

De Silva, R., et al., "Delivery and tracking of therapeutic cell preparations for clinical cardiovascular applications", *Cytotherapy*, 6(6), (2004),608-614.

Eck, S., et al., "Gene-Based Therapy", *Goodman & Gilman's The Pharmacological Basis of Therapeutics*, Chapter 5, Section 1, General Principles, New York; McGraw-Hill,(2001),77-101.

Elisseeff, Jennifer, et al., "Controlled-release of IGF-I and TGF-B1 in a photopolymerizing Hydrogel for cartilage tissue engineering", *Journal of Orthopaedic Research*, vol. 19, (2001),1098-1104.

Gage, H. F., "Cell Therapy", *Nature*, 392, Supp., (Apr. 28, 1998),18-24.

Kofidis, T., et al., "In vitro engineering of heart msucle: Artificial myocardial tissue", *The Journal of Thoracic and Cardiovascular Surgery*, 124 (1), (2002),63-69.

Odorico, S. J., et al., "Multilineage differentiation from human embryonic stem cell lines", *Stem Cells*, 19(3), (2001),193-204.

Parikh, S., et al., "Endothelial Cell Delivery for Cardiovascular Therapy", *Advanced Drug Delivery Reviews*, 42, (2000),139-161.

Pfeifer, A., et al., "Gene Therapy: Promises and Problems", *Ann. Rev. of Genomics and Hum. Genet.*, 2, (2001),177-211.

Samstein, B., et al., "Physiologic and Immunologic Hurdles to Xenotransplantation", *Journal of the American Society of Nephrology*, 12, (2001),182-193.

Srour, E. F., et al., "Ex Vivo Expansion of Hematopoietic Stem and Progenitor Cells: Are We There Yet?", *The Journal of Hematotherapy*, 8, (1999),93-102.

Stolen, Craig, et al., "Method and Apparatus for Preconditioning of Cells", U.S. Appl. No. 11/424,066, filed Jun. 14, 2006, 36 Pages.

Verma, I. M., et al., "Gene Therapy—Promises, Problems and Prospects", *Nature*, 389, (Sep. 18, 1997),239-242.

"U.S. Appl. No. 10/890,825 Final Office Action mailed Jun. 7, 2007", 11 pgs.

"U.S. Appl. No. 10/890,825 Non Final Office Action mailed Jan. 11, 2007.", 15 pgs.

"U.S. Appl. No. 10/890,825 Response filed Apr. 11, 2007 to Non Final Office Action mailed Jan. 11, 2007", 17 pgs.

"U.S. Appl. No. 10/890,825 Response filed Sep. 7, 2007 to Final Office Action mailed Jun. 7, 2007", 22 pgs.

"International Search Report for corresponding PCT Application No. PCT/US2007/003855",(Jul. 5, 2007), 5 pgs.

"Written Opinion for corresponding PCT Application No. PCT/US2007/003855", (Jul. 5, 2007), 7 pgs.

Goodman, R., et al., "Insights into electromagnetic interaction mechanims.", *J Cell Physiol.*, 192(1), (Jul. 2002), 16-22.

Malagoli, D., et al., "50 Hz magnetic fields activate mussel immunocyte p38 MAP kinase and ianduce HSP70 and 90.", *Comp Biochem Physiol C Toxicol Pharmacol.*, 137(1), (Jan. 2004), 75-9.

Tokalov, S. V., et al., "Weak electromagnetic fields (50 Hz) elicit a stress response in human cells", *Environ Res.*, 94(2), (Feb. 2004), 145-51.

"U.S. Appl. No. 10/890,825, Non-Final Office Action mailed Nov. 20, 2007", 10 pgs.

U.S. Appl. No. 10/890,825, Response filed Feb. 20, 2008 to Non-Final Office Action mailed Nov. 20, 2007, 20 pgs.

U.S. Appl. No. 11/017,432, Response filed Mar. 5, 2008 to Non-Final Office Action mailed Nov. 5, 2007, 13 pgs.

Chachques, J. C., et al., "Electrostimulation Enhanced Fatigue Resistant Myosin Expression in Cellular Cardiomyoplasty", *Circulation*, 104(Suppl. 2), (Abstract No. 2626), Abstracts from Scientific Sessions 2001, Anaheim, CA, Nov. 11-14, 2001, II-555-II-556.

Pratt, A. B., et al., "Synthetic Extracellular Matrices for In Situ Tissue Engineering", *Biotechnology and Bioengineering*, 86(1), (2004), 27-36.

Shimizu, et al., "Electrically Communicating Three-Dimensional Cardiac Tissue Mimic Fabricated by Layered Cultured Cardiomyocyte Sheets", *J. Biomedical Materials Research*, 60, (2004), 110-117.

Willey, C. D., et al., "Focal Complex Formation in Adult Cardiomyocytes is Accompanied by the Activation of $\beta 3$ Integrin and c-Src", *Journal of Molecular and Cellular Cardiology*, 35, (2003), 671-683.

Yao, M., et al., "Long-Term Outcome of Fetal Cell Transplantation on Postinfarction Ventricular Remodeling and Function", *Journal of Molecular and Cellular Cardiology*, 35, (2003),661-670.

Zimmermann, W.-H., et al., "Engineered Heart Tissue for Regeneration of Diseased Hearts", *Biomaterials*, 25, (2004),1639-1647.

"U.S. Appl. No. 10/890,825, Non-Final Office Action mailed May 13, 2008", 10 pgs.

Kaye, et al., "Role of Tansiently altered sarcolemmal membrane permeability and basic friboblast growth factor release . . . ", *J.Clin. Invest*. vol. 97, (1996),281-291.

Yamamoto, et al., "Regulation of cardiomyocyte mechanotransduction by the cardiac cycle", *Circulation*. vol. 103, (2001),1459-1564.

"U.S. Appl. No. 10/890,825, Response filed Aug. 11, 2008 to Non Final Office Action mailed May 13, 2008", 18 pgs.

"U.S. Appl. No. 10/890,825, Non-Final Office Action mailed Nov. 14, 2008", 12 pgs.

"U.S. Appl. No. 10/890,825, Response filed Feb. 23, 2009 to Non Final Office Action mailed Nov. 14, 2008", 22 pgs.

"U.S. Appl. No. 11/276,077, Non-Final Office Action mailed Mar. 17, 2009", 11 pgs.

"U.S. Appl. No. 10/890,825, Final Office Action mailed Jun. 22, 2009", 14 pgs.

"U.S. Appl. No. 11/276,077, Response filed Jul. 17, 2009 to Non Final Office Action mailed Mar. 17, 2009", 22 pgs.

"U.S. Appl. No. 10/890,825, Notice of Allowance mailed Jan. 19, 2010", 7 pgs.

"U.S. Appl. No. 10/890,825, Response filed Nov. 6, 2009 to Final Office Action mailed Jun. 22, 2009", 24 pgs.

"U.S. Appl. No. 11/276,077, Final Office Action mailed Nov. 23, 2009", 6 pgs.

"U.S. Appl. No. 11/276,077, Response filed Feb. 23, 2010 to Final Office Action mailed Nov. 23, 2009", 14 pgs.

Bell, E., "Strategy for the Selection of Scaffolds for Tissue Engineering", *Tissue Engineering*, 1(2), (1995), 163-179.

Brightman, A. O., et al., "Time-Lapse Confocal Reflection Microscopy of Collagen Fibrillogenesis and Extracellular Matric Assembly", *Biopolymers*, vol. 54, (2000), 222-234.

Coombes, A. G, et al., "Biocomposites of non-crosslinked natural and synthetic polymers", *Biomaterials*, 23(10), (May 2002), 2113-8.

Everaerts, F., et al., "Quantification of carboxyl groups in carbodiimide cross-linked collagen sponges", *J. Biomed Mater Res A.*, 83(4), (Dec. 15, 2007), 1176-83.

Hodde, J. P, et al., "Retention of endothelial cell adherence to porcine-derived extracellular matrix after disinfection and sterilization", *Tissue Eng.*, 8(2), (Apr. 2002), 225-34.

Petite, H., et al., "Use of diphenylphosphorylazide for cross-linking collagen-based biomaterials", *J Biomed Mater Res.*, 28(2), (Feb. 1994), 159-65.

Rault, I., et al., "Evaluation of different chemical methods for cross-linking collagen gel, films and sponges", *Journal of Materials Science: Materials in Medicine*, 7, (1996), 215-221.

Vaissiere, G., et al., "Comparative analysis of different collagen-based biomaterials as scaffolds for long-term culture of human fibroblasts", *Med Biol Eng Comput.*, 38(2), (Mar. 2000), 205-10.

US 6,875,206, 04/2005, Ponzi (withdrawn)

* cited by examiner

METHOD AND APPARATUS FOR DEVICE CONTROLLED GENE EXPRESSION

FIELD OF THE INVENTION

This invention relates generally to gene therapy of living tissue and particularly, but not by way of limitation, to method and apparatus for regulation of gene expression using a device generating gene transcription triggering signals.

BACKGROUND OF THE INVENTION

The heart is the center of a person's circulatory system. It includes an electromechanical system performing two major pumping functions. The left portions of the heart draw oxygenated blood from the lungs and pump it to the organs of the body to provide the organs with their metabolic needs for oxygen. The right portions of the heart draw deoxygenated blood from the organs and pump it into the lungs where the blood gets oxygenated. The body's metabolic need for oxygen increases with the body's physical activity level. The pumping functions are accomplished by contractions of the myocardium (heart muscles). In a normal heart, the sinoatrial node, the heart's natural pacemaker, generates electrical impulses, known as action potentials, that propagate through an electrical conduction system to various regions of the heart to excite myocardial tissues in these regions. Coordinated delays in the propagations of the action potentials in a normal electrical conduction system cause the various regions of the heart to contract in synchrony such that the pumping functions are performed efficiently.

A blocked or otherwise damaged electrical conduction system causes the myocardium to contract at a rhythm that is too slow, too fast, and/or irregular. Such an abnormal rhythm is generally known as arrhythmia. Arrhythmia reduces the heart's pumping efficiency and hence, diminishes the blood flow to the body. A deteriorated myocardium has decreased contractility, also resulting in diminished blood flow. A heart failure patient usually suffers from both a damaged electrical conduction system and a deteriorated myocardium. The diminished blood flow results in insufficient blood supply to various body organs, preventing these organs to function properly and causing various symptoms. For example, in a patient suffering acute decompensated heart failure, an insufficient blood supply to the kidneys results in fluid retention and edema in the lungs and peripheral parts of the body, a condition referred to as decompensation. Without effective treatment, acute decompensated heart failure cause rapid deterioration of the cardiovascular and general health and significantly shortened life expectancy. Treatments for arrhythmias and heart failure include, but are not limited to, electrical therapy such as pacing and defibrillation therapies, drug therapies, and biological therapies including gene-based therapies.

Gene-based therapies include the delivery of therapeutic genes to targeted cells and in some cases, the use of regulatable systems. For gene-based therapies which require expression of sequences in vectors, a promoter is linked to the sequence to be expressed. Strong viral promoters can drive a high level of expression in a wide range of tissues and cells, however, constitutive expression is an open loop system and the encoded gene product may induce cellular toxicity or tolerance, or down regulation of expression through negative feedback.

One strategy to regulate the expression of target genes employs endogenous regulatable elements, and another strategy employs exogenous inducible gene expression systems. For example, heat-shock-induced loci have been used to regulate the expression of a heterologous gene in mammalian cells (Wurm et al., *Proc. Natl. Acad. Sci. USA,* 83:5414 (1986); Bovenberg et al., *Mol. Cell Endocrinol.,* 74:45 (1990)), and hypoxia-inducible cis-acting sequences from the erythropoietin gene allow a transcriptional response by hypoxia-inducible transcription factor (HIF-I) (Wang et al., *Curr. Op. Hematol.,* 3:156 (1996)). However, many regulatable systems based on endogenous promoters suffer from weak induction and high basal expression.

What is needed is a device useful to control expression of gene therapy vectors, e.g., to treat cardiovascular conditions.

SUMMARY OF THE INVENTION

The present invention provides spatial, temporal and/or conditional control of gene expression from one or more gene therapy vectors via an implantable device. The gene therapy vector includes one or more gene sequences useful to alter, for instance, enhance or inhibit, expression of one or more native (endogenous) genes or the corresponding encoded gene product(s), or expression of one or more nonnative genes or the corresponding encoded gene product(s), in cells, which expression in vivo prevents, inhibits or treats at least one symptom of a particular condition. Thus, for a condition in which expression of a native gene is aberrant, e.g., results in lack of or low expression of a functional gene product or overexpression of a functional gene product, or the native gene product lacks or has aberrant activity, the gene therapy vector includes an open reading frame for a gene operably linked to at least one regulatable transcriptional control element, the expression of which open reading frame in cells in an organism is effective to prevent, inhibit or treat at least one symptom of a particular condition. In one embodiment, for conditions in which it is desirable to inhibit expression of a native gene or gene product, the gene therapy vector may include an appropriate antisense gene sequence or a mutant gene, e.g., one which encodes a dominant negative gene product, operably linked to at least one regulatable transcriptional control element. In another embodiment, for conditions in which it is desirable to express or augment expression of a gene or gene product, the gene therapy vector may include an appropriate gene sequence or a portion thereof (sense orientation), i.e., a portion that encodes a gene product with substantially the same activity as the full length gene product, operably linked to at least one regulatable transcriptional control element. In one embodiment, the condition is a cardiac condition and the expression of the gene(s) in the gene therapy vector in an animal, such as a mammal, having or at risk of the cardiac condition, alters the electrophysiologic properties in a defined region of the heart.

To control expression of the gene(s) in the gene therapy vector(s) once the vector(s) are administered to an animal, an implantable device is employed. The device may be introduced to the animal before, concurrent with or after the gene therapy vector(s) are administered. In one embodiment, the vector(s) which are delivered are not associated with an intact cell, e.g., a recombinant virus or isolated DNA having a desirable gene sequence is administered to the animal. In another embodiment, recombinant cells which include the gene therapy vector(s) are employed, e.g., cells useful to express secreted proteins or useful in cell therapy. The implantable device includes a controller which emits a signal upon sensing a physiological parameter or a change in a physiological parameter, or as a result of an external command, the amount and/or strength of which signal alters expression, e.g., induces expression, of the gene that is operably linked to the regulatable transcriptional control element in the gene therapy vector. Thus, the systems and methods of the invention which employ sensors and diagnostic information allow for control of gene therapy, thus providing for spatial, temporal and/or conditional dosing of the gene product encoded by the gene therapy vector(s) in an animal. Hence, titration of the dose administered is readily accomplished.

The invention thus provides a method to control expression of at least one exogenously introduced expression cassette which includes a regulatable transcriptional control element operably linked to an open reading frame in an animal at risk of a cardiac condition. The method includes providing an animal at risk of the cardiac condition which comprises a system of the invention, e.g., a system which includes a sensor to sense a physiological signal indicative of a predetermined cardiac condition, a gene regulatory signal delivery device that emits a regulatory signal which directly or indirectly regulates a regulatable transcriptional control element, and a controller coupled to the sensor and the gene regulatory signal delivery device, the controller adapted to control the emission of the regulatory signal based on at least the sensed physiological signal. At least one expression cassette that is introduced to the animal includes a transcriptional control element, which is directly or indirectly regulated by the emitted signal, operably linked to an open reading frame. In response to detection of the condition, a signal is emitted from the system so as to control expression of the open reading frame. The expression of the open reading frame in the animal prevents, inhibits or treats the condition or at least one symptom thereof.

Also provided is a method to control expression of at least one exogenously introduced expression cassette which includes a regulatable transcriptional control element operably linked to an open reading frame in an animal at risk of a cardiac condition. The method includes providing an animal comprising at least one exogenously introduced expression cassette that includes a transcriptional control element, which is directly or indirectly regulated by a signal, operably linked to an open reading frame, the expression of which is capable of preventing, inhibiting or treating a cardiac condition or at least one symptom thereof in an animal at risk of the cardiac condition. A system of the invention is introduced to the animal, and in response to detection of the condition, a signal is emitted from the system so as to control expression of the open reading frame. The expression of the open reading frame in the animal prevents, inhibits or treats the condition or at least one symptom thereof.

In one embodiment, the invention provides a method to prepare an implantable device effective to control expression of at least one exogenously introduced expression cassette which includes a regulatable transcriptional control element operably linked to an open reading frame in an animal at risk of a cardiac condition. The method includes introducing to an implantable device a gene regulatory signal delivery device that emits a regulatory signal which directly or indirectly regulates the transcriptional control element. The expression of the open reading frame in the at least one exogenously introduced expression cassette is capable of preventing, inhibiting or treating the condition or at least one symptom thereof.

In one embodiment, a mammal has heart failure and is contacted with a gene therapy vector having a Serca2A gene operably linked to a phytochrome promoter. The mammal is also contacted with an implantable device which detects decreased cardiac function, e.g., decreased heart rate variability (HRV). Upon detection of decreased cardiac function, the implantable device emits light which induces expression from the phytochrome promoter. For instance, the device emits an appropriate signal via a fiber optic or LED. The light signal is emitted so as to express the Serca2A gene in the gene therapy vector in an amount effective to enhance cardiac function. In another embodiment, a mammal has heart failure and is contacted with a gene therapy vector having a β-adrenergic signaling protein gene operably linked to a promoter sensitive to a subthreshold (below threshold for muscular excitation), threshold, or suprathreshold voltage, or a combination thereof, e.g., a MT-1 promoter. The mammal is also contacted with an implantable device which detects decreased cardiac function. Upon detection of decreased cardiac function, the implantable device emits a voltage which induces expression from the promoter. The signal is emitted so as to express the β-adrenergic signaling protein gene in the gene therapy vector in an amount effective to enhance cardiac function. In one embodiment, the signal emitted from the device induces expression of the gene and provides for electrical therapy, e.g., pacing or defibrillation. In yet another embodiment, a mammal suffers from atrial fibrillation and is contacted with a gene therapy vector having a Kir2.1 gene operably linked to a thermal sensitive promoter. The mammal is contacted with an implantable device which detects atrial electrogram. Upon detection of an atrial arrhythmia, the implantable device emits heat and Kir2.1 is expressed from the gene therapy vector in an amount effective to terminate atrial fibrillation. For example, once sinus rhythm is restored, the heat signal emitted from the device is terminated. Thus, the systems of the invention provide for feedback control of gene therapy.

BRIEF DESCRIPTION OF THE DRAWINGS

The drawings illustrate generally, by way of example, but not by way of limitation, various embodiments discussed in the present document. The drawing are for illustrative purposes only and are not drawn to scale.

DETAILED DESCRIPTION OF THE INVENTION

Figure 1:
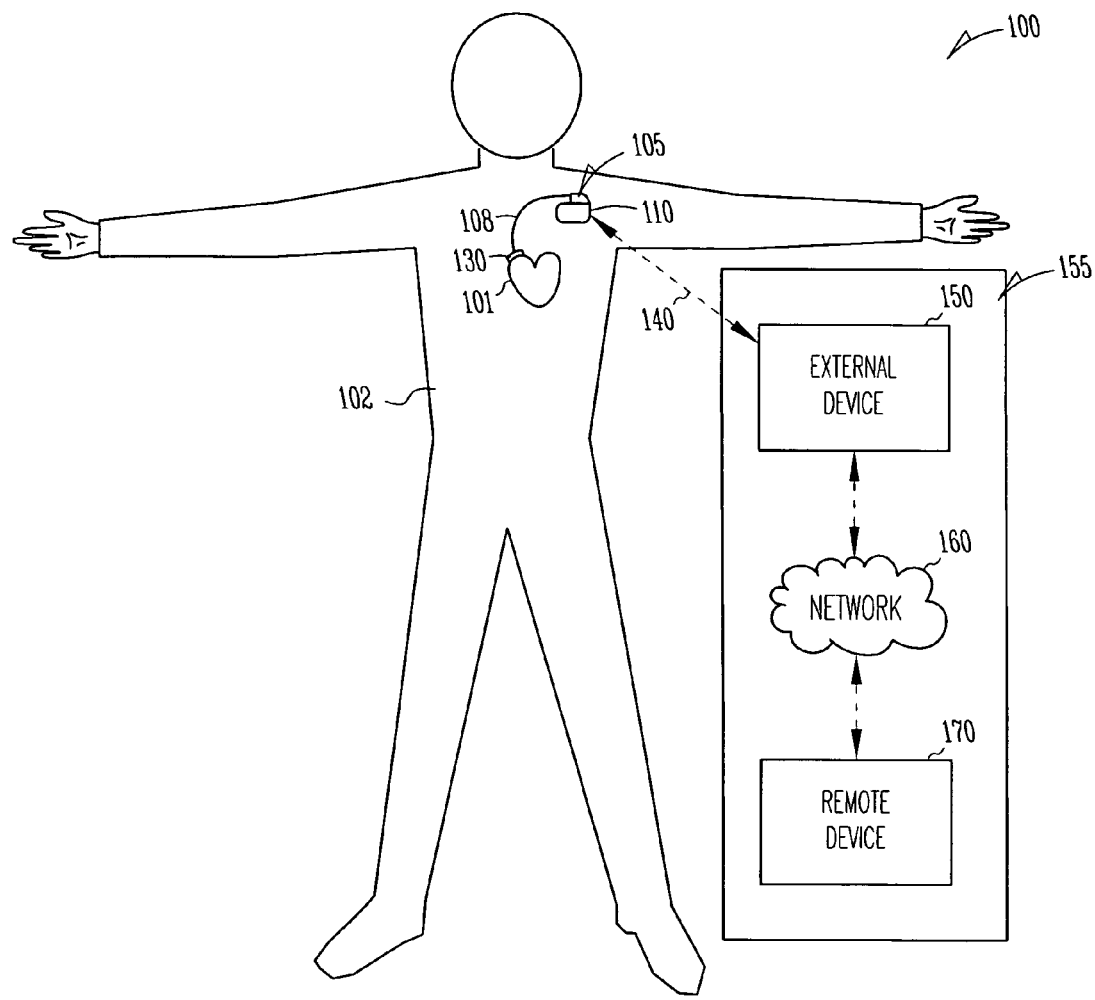
FIG. 1 is an illustration of an embodiment of a gene regulatory system and portions of an environment in which it is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

General Overview

This document describes, among other things, methods and apparatus for the control of gene therapy. In one embodiment, a mammal having or at risk of having a particular condition, e.g., a cardiovascular condition, is subjected to gene therapy which is intended to inhibit, prevent or treat one or more symptoms associated with the condition. The gene therapy vector encodes at least one therapeutic gene product and is operably linked to at least one regulatable transcriptional control element, forming an expression cassette. In one embodiment, the gene therapy vector includes at least one transgene that encodes a gene product including, but not limited to, an angiogenic protein, a growth factor, a differentiation factor, a survival factor, a cytokine, a cardiac cell-specific structural gene product, a cardiac cell-specific transcription factor, or a membrane protein, e.g., a gap junction or an ion channel protein, or including an antisense sequence, for instance, a ribozyme or antisense oligonucleotide, or any combination thereof. The expression of the gene product is under the control of a regulatable transcriptional control element such as a promoter, e.g., an inducible or repressible promoter, or an enhancer. For instance, the enhancer may be a glucocorticoid responsive enhancer or the promoter may be an electromagnetic responsive promoter. In one embodiment, the expression of the gene is also disease-, cell- or tissue-specific, e.g., cardiac cell-specific, due to a disease-, cell- or tissue-specific promoter and/or enhancer. For instance, the enhancer may be a muscle creatine kinase (mck) enhancer, or the promoter may be an alpha-myosin heavy chain (MyHC) or beta-MyHC promoter (see Palermo et al., *Circ. Res.*, 78, 504 (1996)). In one embodiment, the transcriptional regulatory element is upregulated by certain disease states, e.g., to treat heart failure or left bundle blockage, a vector of the invention may include a transcriptional regulatory element from a gene that is upregulated in patients having heart failure or upregulated during progression of heart failure, e.g., transcriptional regulatory elements from genes including but not limited to those for an extracellular signal-regulated kinase (ERK), mitogen-activated protein kinase (MAPK), stress activated protein kinase (SAPK), p38, calcineurin, Akt, $Na^+$/$Ca^{2+}$ exchanger (NCX), metal metalloproteinase-2 (MMP-2) or MMP-7. To treat atrial fibrillation, a vector of the invention may include a transcriptional regulatory element from a gene that is upregulated in patients having atrial fibrillation, e.g., genes associated with the production of reactive oxygen species (ROS) including flavin containing monooxygenase I, monoamine oxidase B, ubiquitin specific protease 8, tyrosinase-related protein 1, tyrosine 3 related monoxygenase, MMP-2 or MMP-7. To treat systolic dysfunction, a vector of the invention may include a transcriptional regulatory element from a gene such as the one encoding the $Na^+$/$Ca^{2+}$ exchanger. Optionally, a combination of gene therapy vectors, each with a different transgene and at least one of which includes a regulatable transcriptional control element, is employed.

Prior to, concurrent with or after gene therapy, an implantable device which regulates expression of the gene(s) in the gene therapy vector is provided to the animal. In one embodiment, the device is introduced at or near damaged cardiovascular tissue. In response to detection of a symptom of a condition, e.g., a change in a physiological parameter such as heart rate, the device emits a signal which activates the regulatable transcriptional control element in the gene therapy vector. Such signals include, but are not limited to, an electric field, electromagnetic field, light, sound, temperature, and/or chemical agents such as a biologic agent (i.e., one encoded by DNA) or a nonbiologic agent, e.g., a beta adrenergic blocker, an alpha adrenergic blocker, a calcium channel blocker, an ACE inhibitor or an angiotension II blocker. In one embodiment, after expression from the gene therapy vector is induced and a desirable change in the physiological parameter detected, the signal is discontinued. In another embodiment, the signal is emitted for a predetermined time period. Thus, gene expression may be turned on and off or titrated by controlling signals emitted by the device.

Thus, this document discusses a gene regulatory system that includes an implantable gene regulatory signal delivery device being a portion of, or being coupled to, an implantable medical device. In one embodiment, the implantable medical device detects a predetermined condition indicative of a need for a therapy. In response, the implantable gene regulatory signal delivery device delivers one or more signals. In one further embodiment, the gene regulatory therapy is performed in conjunction with electrical therapy, such as pacing therapy, and/or drug therapy. One specific example of the implantable medical device is an implantable cardiac rhythm management (CRM) device. Though discussed specifically in this document as part of a CRM system, the gene regulatory system is generally usable for all in vivo gene therapies. Several embodiments are presented below to provide examples of different therapy apparatus and method.

Definitions

A "vector" or "construct" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a sequence of interest for gene therapy. Vectors include, for example, transposons and other site-specific mobile elements, viral vectors, e.g., adenovirus, adeno-associated virus (AAV), poxvirus, papillomavirus, lentivirus, herpesvirus, foamivirus and retrovirus vectors, and including pseudotyped viruses, liposomes and other lipid-containing complexes, and other macromolecular complexes capable of mediating delivery of a polynucleotide to a host cell, e.g., DNA coated gold particles, polymer-DNA complexes, liposome-DNA complexes, liposome-polymer-DNA complexes, virus-polymer-DNA complexes, e.g., adenovirus-polylysine-DNA complexes, and antibody-DNA complexes. Vectors can also comprise other components or functionalities that further modulate gene delivery and/or gene expression, or that otherwise provide beneficial properties to the cells to which the vectors will be introduced. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

A "recombinant viral vector" refers to a viral vector comprising one or more heterologous genes or sequences. Since many viral vectors exhibit size constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation). Modified viral vectors in which a polynucleotide to be delivered is carried on the outside of the viral particle have also been described (see, e.g., Curiel et al., *Proc. Natl. Acad. Sci. USA*, 88:8850 (1991)).

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, iontophoresis, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art.

By "transgene" is meant any piece of a nucleic acid molecule (for example, DNA) which is inserted by artifice into a cell either transiently or permanently, and becomes part of the organism if integrated into the genome or maintained extrachromosomally. Such a transgene may include a gene which is partly or entirely heterologous (i.e., foreign) to the transgenic organism, or may represent a gene homologous to an endogenous gene of the organism.

By "transgenic cell" is meant a cell containing a transgene. For example, a stem cell transformed with a vector containing an expression cassette can be used to produce a population of cells having altered phenotypic characteristics.

The term "wild-type" refers to a gene or gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

A "disease allele" refers to an allele of a gene that is capable of producing a recognizable disease. However, not all conditions or populations having a certain condition have a known disease allele. A disease allele may be dominant or recessive and may produce disease directly or when present in combination with a specific genetic background or pre-existing pathological condition. A disease allele may be present in the gene pool (an inherited disease allele) or may be generated de novo in an individual by somatic mutation (an acquired disease allele).

"Vasculature" or "vascular" are terms referring to the system of vessels carrying blood (as well as lymph fluids) throughout the mammalian body.

"Blood vessel" refers to any of the vessels of the mammalian vascular system, including arteries, arterioles, capillaries, venules, veins, sinuses, and vasa vasorum.

"Artery" refers to a blood vessel through which blood passes away from the heart. Coronary arteries supply the tissues of the heart itself, while other arteries supply the remaining organs of the body. The general structure of an artery consists of a lumen surrounded by a multi-layered arterial wall.

The term "transduction" denotes the delivery of a polynucleotide to a recipient cell either in vivo or in vitro, via a viral vector and preferably via a replication-defective viral vector, such as via a recombinant AAV.

The term "heterologous" as it relates to nucleic acid sequences such as gene sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature, i.e., a heterologous promoter. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention.

By "DNA" is meant a polymeric form of deoxyribonucleotides (adenine, guanine, thymine, or cytosine) in double-stranded or single-stranded form found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the nontranscribed strand of DNA (i.e., the strand having the sequence complementary to the mRNA). The term captures molecules that include the four bases adenine, guanine, thymine, or cytosine, as well as molecules that include base analogues which are known in the art.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

A "gene," "polynucleotide," "coding region," or "sequence" which "encodes" a particular gene product, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. Thus, a gene includes a polynucleotide which may include a full-length open reading frame which encodes a gene product (sense orientation) or a portion thereof (sense orientation) which encodes a gene product with substantially the same activity as the gene product encoded by the full-length open reading frame, the complement of the polynucleotide, e.g., the complement of the full-length open reading frame (antisense orientation) and optionally linked 5' and/or 3' noncoding sequence(s) or a portion thereof, e.g., an oligonucleotide, which is useful to inhibit transcription, stability or translation of a corresponding mRNA. A transcription termination sequence will usually be located 3' to the gene sequence.

An "oligonucleotide" includes at least 7 nucleotides, preferably 15, and more preferably 20 or more sequential nucleotides, up to 100 nucleotides, either RNA or DNA, which correspond to the complement of the non-coding strand, or of the coding strand, of a selected mRNA, or which hybridize to the mRNA or DNA encoding the mRNA and remain stably bound under moderately stringent or highly stringent conditions, as defined by methods well known to the art, e.g., in Sambrook et al., A Laboratory Manual, Cold Spring Harbor Press (1989).

The term "control elements" refers collectively to promoter regions, polyadenylation signals, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence. Thus, a "promoter," refers to a polynucleotide sequence that controls transcription of a gene or coding sequence to which it is operably linked. A large number of promoters, including constitutive, inducible and repressible promoters, from a variety of different sources, are well known in the art.

By "enhancer element" is meant a nucleic acid sequence that, when positioned proximate to a promoter, confers increased transcription activity relative to the transcription activity resulting from the promoter in the absence of the enhancer domain. Hence, an "enhancer" includes a polynucleotide sequence that enhances transcription of a gene or coding sequence to which it is operably linked. A large number of enhancers, from a variety of different sources are well known in the art. A number of polynucleotides which have promoter sequences (such as the commonly-used CMV promoter) also have enhancer sequences.

By "cardiac-specific enhancer or promoter" is meant an element, which, when operably linked to a promoter or alone, respectively, directs gene expression in a cardiac cell and does not direct gene expression in all tissues or all cell types. Cardiac-specific enhancers or promoters may be naturally occurring or non-naturally occurring. One skilled in the art will recognize that the synthesis of non-naturally occurring enhancers or promoters can be performed using standard oligonucleotide synthesis techniques.

"Operably linked" refers to a juxtaposition, wherein the components so described are in a relationship permitting them to function in their intended manner. By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. A promoter is operably linked to a coding sequence if the promoter controls transcription of the coding sequence. Although an operably linked promoter is generally located upstream of the coding sequence, it is not necessarily contiguous with it. An enhancer is operably linked to a coding sequence if the enhancer increases transcription of the coding sequence. Operably linked enhancers can be located upstream, within or downstream of coding sequences. A polyadenylation sequence is operably linked to a coding sequence if it is located at the downstream end of the coding sequence such that transcription proceeds through the coding sequence into the polyadenylation sequence. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. Thus, a signal or targeting peptide sequence is operably linked to another protein if the resulting fusion is secreted from a cell as a result of the presence of a secretory signal peptide or into an organelle as a result of the presence of an organelle targeting peptide.

"Homology" refers to the percent of identity between two polynucleotides or two polypeptides. The correspondence between one sequence and to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like. An "animal" includes vertebrates such as mammals, avians, amphibians, reptiles and aquatic organisms including fish.

By "derived from" is meant that a nucleic acid molecule was either made or designed from a parent nucleic acid molecule, the derivative retaining substantially the same functional features of the parent nucleic acid molecule, e.g., encoding a gene product with substantially the same activity as the gene product encoded by the parent nucleic acid molecule from which it was made or designed.

By "expression construct" or "expression cassette" is meant a nucleic acid molecule that is capable of directing transcription. An expression construct includes, at the least, a promoter. Additional elements, such as an enhancer, and/or a transcription termination signal, may also be included.

The term "exogenous," when used in relation to a protein, gene, nucleic acid, or polynucleotide in a cell or organism refers to a protein, gene, nucleic acid, or polynucleotide which has been introduced into the cell or organism by artificial or natural means, or in relation a cell refers to a cell which was isolated and subsequently introduced to other cells or to an organism by artificial or natural means. An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

The term "isolated" when used in relation to a nucleic acid, peptide, polypeptide or virus refers to a nucleic acid sequence, peptide, polypeptide or virus that is identified and separated from at least one contaminant nucleic acid, polypeptide, virus or other biological component with which it is ordinarily associated in its natural source. Isolated nucleic acid, peptide, polypeptide or virus is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded).

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "peptide", "polypeptide" and protein" are used interchangeably herein unless otherwise distinguished to refer to polymers of amino acids of any length. These terms also include proteins that are post-translationally modified through reactions that include glycosylation, acetylation and phosphorylation.

By "growth factor" is meant an agent that, at least, promotes cell growth or induces phenotypic changes.

The term "angiogenic" means an agent that alone or in combination with other agents induces angiogenesis, and includes, but is not limited to, fibroblast growth factor (FGF), vascular endothelial growth factor (VEGF), hepatocyte growth factor, angiogenin, transforming growth factor (TGF), tissue necrosis factor (TNF, e.g., TNF-α), platelet derived growth factor (PDGF), granulocyte colony stimulatory factor (GCSF), placental GF, IL-8, proliferin, angiopoietin, e.g., angiopoietin-1 and angiopoietin-2, thrombospondin, ephrin-A1, E-selectin, leptin and heparin affinity regulatory peptide.

"Gene regulation" or "Gene regulatory therapy" as used herein includes delivery of one or more gene regulatory signals to regulate gene expression in a gene therapy vector. The gene regulatory signals include signals that trigger a transcriptional control element, e.g., a promoter.

A "user" includes a physician or other caregiver using a gene regulatory system to treat a patient.

Apparatus

FIG. 1 is an illustration of an embodiment of a gene regulatory system 100 and portions of an environment in which it is used. System 100 includes implantable system 105, external system 155, and telemetry link 140 providing for communication between implantable system 105 and external system 155.

Implantable system 105 includes, among other things, implantable CRM device 110, lead system 108, and implantable gene regulatory signal delivery device 130. As shown in FIG. 1, implantable CRM device 110 is implanted in a body 102. In one embodiment, implantable CRM device 110 includes a gene regulatory controller. In one embodiment, implantable gene regulatory signal delivery device 130 delivers one or more gene regulatory signals to heart 101. In another embodiment, implantable gene regulatory signal delivery device 130 delivers one or more gene regulatory signals to the vascular system of body 102, such as a vein. In various other embodiments, implantable gene regulatory signal delivery device 130 delivers one or more gene regulatory signals to any site within body 102 targeted for the gene regulatory therapy. Lead system 108 provides for access to one or more locations to which the regulatory one or more gene regulatory signals are delivered. In one embodiment, lead system 108 includes one or more leads providing for electrical connections between implantable CRM device 110 and implantable gene regulatory signal delivery device 130. In another embodiment, lead system 108 provides for the transmission of the one or more gene regulatory signals to the locations to which the signals are delivered. In various embodiments, implantable CRM device 110 also includes a pacemaker, a cardioverter/defibrillator, a cardiac resynchronization therapy (CRT) device, a cardiac remodeling control therapy (RCT) device, a drug delivery device or a drug delivery controller, a cell therapy device, or any other implantable medical device. Lead system 108 further includes leads for sensing physiological signals and delivering pacing pulses, cardioversion/defibrillation shocks, and/or pharmaceutical or other substances.

External system 155 includes external device 150, network 160, and remote device 170. External device 150 is within the vicinity of implantable CRM device 110 and communicates with implantable CRM device 110 bi-directionally via telemetry link 140. Remote device 170 is in a remote location and communicates with external device 150 bi-directionally via network 160, thus allowing a user to monitor and treat a patient from a distant location.

System 100 allows a delivery of a gene regulatory therapy, i.e., delivery of the one or more gene regulatory signals, to be triggered by any one of implantable CRM device 110, external device 150, and remote device 170. In one embodiment, implantable CRM device 110 triggers the delivery of the gene regulatory therapy upon detecting a predetermined signal or condition. In another embodiment, external device 150 or remote device 170 triggers the delivery of the gene regulatory therapy upon detecting an abnormal condition from a signal transmitted from implantable CRM device 110. In one specific embodiment, external system 155 includes a processor running a therapy decision algorithm to determine whether and when to trigger the delivery of the gene regulatory therapy. In another specific embodiment, external system 155 includes a user interface to present signals acquired by implantable CRM device 155 and/or the detected abnormal condition to a user and receives commands from the user for triggering the delivery of the gene regulatory therapy. In another specific embodiment, the user interface includes a user input incorporated into external device 150 to receive commands from the user and/or the patient treated with system 100. For example, the patient may be instructed to enter a command for the gene regulatory therapy when he senses certain symptoms, and another person near the patient may do the same upon observing the symptoms.

It is to be understood that an implantable gene regulatory signal delivery device and an implantable CRM device are discussed to illustrate, but not to restrict, the present subject matter. Though discussed specifically as part of a CRM system, the gene regulatory system and method discussed in this document is generally usable for all in vivo gene therapies delivered by implantable or external devices.

Figure 2:
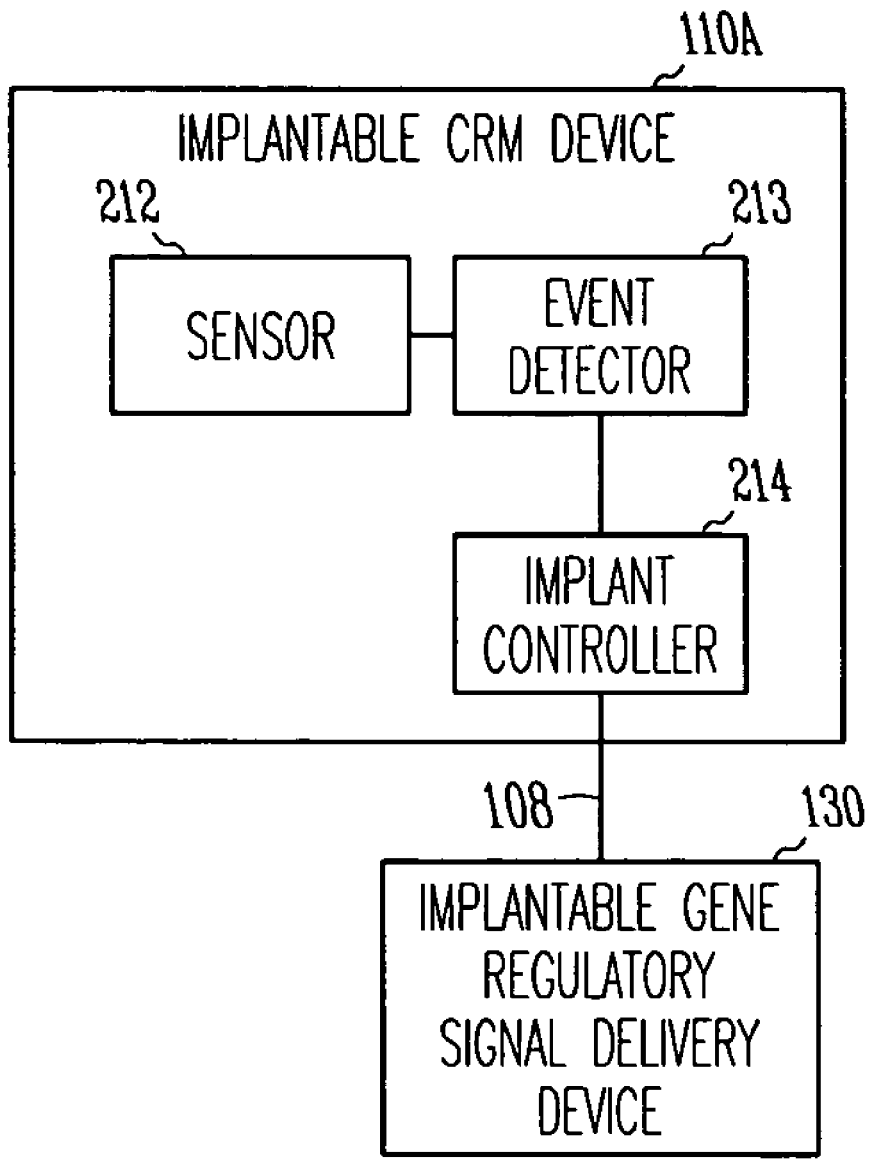
FIG. 2 is a block diagram showing one embodiment of a circuit of portions of the gene regulatory system such as shown in FIG. 1.

FIG. 2 is a block diagram showing one embodiment of the circuit of portions of system 100 including implantable CRM device 110A, lead system 108, and implantable gene regulatory signal delivery device 130. Implantable CRM device 110A represents one specific embodiment of implantable CRM device 110. In one embodiment, lead system 108 provides for an electrical connection between implantable CRM device 110A and implantable gene regulatory signal delivery device 130, such that implantable CRM device transmits a voltage or current signal to control the delivery of a gene regulatory signal.

Implantable gene regulatory signal delivery device 130 receives a gene regulatory control signal from implant controller 214 and, in response, delivers one or more gene regulatory signals in one or more forms of energy being external factors regulating one or more gene expressions. The forms of energy include electrical energy, electromagnetic energy, optical energy, acoustic energy, thermal energy, and any other forms of energy that triggers the gene promoter system. In one embodiment, implantable gene regulatory signal delivery device 130 delivers the one or more gene regulatory signals to the heart. In one specific embodiment, implantable gene regulatory signal delivery device 130 is an implantable device designed for placement within the heart. In another embodiment, implantable gene regulatory signal delivery device 130 delivers the one or more gene regulatory signals to the blood. In one specific embodiment, implantable gene regulatory signal delivery device 130 is an implantable device designed for placement within with the vascular system, such as in a vein.

In one embodiment, implantable gene regulatory signal delivery device 130 includes an electric field generator that generates and emits an electric field. The electric field has predetermined frequency and strength selected for regulating gene expression in an exogenously introduced vector. In one specific embodiment, an electric field generator includes electrodes to which a voltage is applied. The intensity of the electric field is controlled by controlling the voltage across the electrodes.

In one embodiment, implantable gene regulatory signal delivery device 130 includes an electromagnetic field generator that generates and emits an electromagnetic field. The electromagnetic field has predetermined frequency and strength selected for regulating gene expression in an exogenously introduced vector. In one specific embodiment, the electromagnetic field generator includes an inductive coil. The intensity of the electromagnetic field is controlled by controlling the voltage across the coil and/or the current flowing through it. In one specific embodiment, the electromagnetic field has a frequency of about 1 Hz to 1 KHz. In another specific embodiment, the electromagnetic field is a direct-current (dc) electromagnetic field.

In one embodiment, implantable gene regulatory signal delivery device 130 includes an optical emitter that emits light. The light has predetermined wavelength or band of wavelengths and intensity selected for regulating gene expression. In one specific embodiment, the optical emitter includes a light-emitting diode (LED). The intensity of the light is controlled by controlling the voltage across the LED and/or the current flowing through it. In another specific embodiment, the optical emitter includes an array of LEDs that can be programmed to emit lights having one or more distinct wavelengths.

In one embodiment, implantable gene regulatory signal delivery device 130 includes a speaker that emits a sound. The sound has a predetermined frequency and intensity selected for regulating gene expression in an exogenously introduced vector.

In one embodiment, implantable gene regulatory signal delivery device 130 includes a drug delivery device which emits one or more chemical agents. The one or more chemical agents have properties known to regulate expression from a transcriptional control element. Examples of the one or more chemical agents include chemicals which induce expression from a particular promoter, including tetracycline, rapamycin, auxins, metals and ecdysone.

In one embodiment, implantable gene regulatory signal delivery device 130 includes a thermal radiator that emits a thermal energy. The thermal energy changes the tissue temperature to a point or range suitable for regulating gene expression in an exogenously introduced vector. In one specific embodiment, the thermal radiator includes a resistive element that is heated as an electrical current flows through it or as a voltage is applied across it. The tissue temperature is controlled by controlling the amplitude of the electrical current or voltage.

Implantable CRM device 110A includes sensor 212, event detector 213, and implant controller 214. Sensor 212 senses a physiological signal indicative of an abnormal condition treatable by a gene regulatory therapy administered through implantable gene regulatory signal delivery device 130. Event detector 213 detects that abnormal condition. Implant controller 214 produces and transmits the gene regulatory control signal to implantable gene regulatory signal delivery device 130 to trigger a delivery of the gene regulatory therapy in response to a detected abnormal condition. In one embodiment, the gene regulatory therapy is delivered for a predetermined period of delivery time. In one specific embodiment, implant controller 214 includes a timer to time the predetermined period of delivery time and produces and transmits a gene regulatory stop signal to implantable gene regulatory signal delivery device 130 to stop the delivery of the gene regulatory therapy. In another specific embodiment, implantable gene regulatory signal delivery device 130 includes a timer to time the predetermined period of delivery time and stops the delivery of the gene regulatory therapy when the predetermined period of delivery time expires. In another embodiment, implant controller 214 produces and transmits the gene regulatory stop signal to implantable gene regulatory signal delivery device 130 to stop the delivery of the gene regulatory therapy after the abnormal condition is no longer detected by event detector 213. In another embodiment, implant controller 214 produces and transmits the gene regulatory stop signal to implantable gene regulatory signal delivery device 130 to stop the delivery of the gene regulatory therapy in response to a command from the user or patient. In one embodiment, event detector 213 further comprising an event parameter generator to produce one or more parameters related to at least one of a type and a degree of the abnormal condition. Implant controller 214 includes a regulatory signal parameter controller to quantitatively control the emission of the regulatory signal based the one or more parameters produced by the event parameter generator. In this embodiment, the gene regulatory control signal includes parameters defining the gene regulatory therapy to be delivered. The parameters include type(s) and quantitative parameters, depending on the type(s), such as electric field strength, electromagnetic field strength and frequency, light intensity and wavelength, sound intensity and frequency, type and amount of chemical, and/or amount of thermal energy.

In one embodiment, sensor 212 includes a cardiac sensing circuit that senses an electrogram, and event detector 213 detects an arrhythmia. In one embodiment, event detector 213 detects the arrhythmia by detecting heart rate and comparing the heart rate to one or more threshold rates. A bradycardia condition is detected when the heart rate falls below a bradycardia threshold. A tachycardia condition is detected when the heart rate exceeds a tachycardia threshold. In a further embodiment, event detector 213 detects the arrhythmia also by detecting morphological features of the electrogram to one or more predetermined templates. In one specific embodiment, event detector 213 includes an atrial fibrillation detector. In one specific embodiment, event detector 213 includes a ventricular fibrillation detector.

In one embodiment, sensor 212 senses a physiological signal indicative of ischemia, and event detector 213 includes an ischemia detector. In one specific embodiment, sensor 212 senses an electrogram and event detector 213 runs an automatic ischemia detection algorithm to detect an ischemic condition from the electrogram. One specific example of an electrogram-based ischemia detector is discussed in Zhu et al., U.S. patent application Ser. No. 09/962,852, entitled "EVOKED RESPONSE SENSING FOR ISCHEMIA DETECTION," filed on Sep. 25, 2001, assigned to Cardiac Pacemakers, Inc., which is incorporated herein by reference in its entirety. In another embodiment, sensor 212 includes an electrical impedance based sensor using a low carrier frequency (e.g., 100 Hz), and event detector 213 runs an automatic ischemia detection algorithm to detect an ischemic condition from the electrical impedance signal. Tissue electrical impedance has been shown to increase significantly during ischemia, as discussed in Min, et al. *International Journal of Bioelectromagnetism,* 5(1): 53 (2003). Sensor 212 senses low frequency electrical impedance signal between electrodes interposed in the heart. Event detector 213 detects the ischemia as abrupt changes in impedance (such as abrupt increases in value). In another specific embodiment, sensor 212 includes a local heart motion based sensor utilizing an accelerometer located within a lead body positioned on or in the heart, and event detector 213 runs an automatic ischemia detection algorithm to detect an ischemic condition from the acceleration signal. Event detector 213 detects ischemia as an abrupt decrease in the amplitude of local cardiac accelerations.

In one embodiment, sensor 212 includes a metabolic sensor that senses a metabolic signal indicative of a cardiac metabolic level (rate of metabolism of cardiac cells). Examples of the metabolic sensor include a pH sensor, an oxygen pressure ($PO_2$) sensor, a carbon dioxide pressure ($PCO_2$) sensor, a glucose sensor, a creatine sensor, a C-creative protein sensor, a creatine kinase sensor, a creatine kinase-MB sensor, and any combination of such sensors. Event detector 213 determines the cardiac metabolic level from the metabolic signal and compares the cardiac metabolic level to one or more predetermined thresholds defining a normal cardiac metabolic range. The abnormal condition is detected when the cardiac metabolic level is outside of the normal cardiac metabolic range.

In one embodiment, sensor 212 includes an impedance sensor to measure pulmonary impedance, or impedance of a portion of the thoracic cavity. Event detector 213 detects the abnormal condition when the impedance is out of its normal range. For example, pulmonary edema, i.e., fluid retention in the lungs resulting from the decreased cardiac output, increases the pulmonary or thoracic impedance. In one specific embodiment, event detector 213 produces the alert signal when the pulmonary or thoracic impedance exceeds a predetermined threshold impedance. In one embodiment, the impedance sensor is a respiratory sensor that senses the patient's minute ventilation. An example of an impedance sensor sensing minute ventilation is discussed in U.S. Pat. No. 6,459,929, "IMPLANTABLE CARDIAC RHYTHM MANAGEMENT DEVICE FOR ASSESSING STATUS OF CHF PATIENTS," assigned to Cardiac Pacemakers, Inc., which is incorporated herein by reference in its entirety.

In one embodiment, sensor 212 includes a pressure sensor. Abnormal conditions including arrhythmias and heart failure cause pressures in various portions of the cardiovascular system to deviate from their normal ranges. Event detector 213 detects the abnormal condition when a pressure is outside of its normal range. In one specific embodiment, event detector 213 includes a systolic dysfunction detector to detect an abnormal condition related to pressure during the systolic phase of a cardiac cycle. In another specific embodiment, event detector 213 includes a diastolic dysfunction detector to detect an abnormal condition related to pressure during the diastolic phase of a cardiac cycle. Examples of the pressure sensor include but are not limited to a left atrial (LA) pressure sensor, a left ventricular (LV) pressure sensor, an artery pressure sensor, and a pulmonary artery pressure sensor. Pulmonary edema results in elevated LA and pulmonary arterial pressures. A deteriorated LV results in decreased LV and arterial pressures. In various embodiments, event detector 213 detects an abnormal condition when the LA pressure exceeds a predetermined threshold LA pressure level, when the pulmonary arterial pressure exceeds a predetermined threshold pulmonary arterial pressure level, when the LV pressure falls below a predetermined threshold LV pressure level, and/or when the arterial pressure falls below a predetermined threshold LV pressure level. In other embodiments, event detector 213 derives a parameter from one of these pressures, such as a rate of change of a pressure, and produces a signal when the parameter deviates from its normal range. In one embodiment, the LV pressure sensor senses the LV pressure indirectly, by sensing a signal having known or predictable relationships with the LV pressure during all or a portion of the cardiac cycle. Examples of such a signal include but are not limited to an LA pressure and a coronary vein pressure. One specific example of measuring the LV pressure using a coronary vein pressure sensor is discussed in U.S. patent application Ser. No. 10/038,936, "METHOD AND APPARATUS FOR MEASURING LEFT VENTRICULAR PRESSURE," filed on Jan. 4, 2002, assigned to Cardiac Pacemakers, Inc., which is hereby incorporated by reference in its entirety.

In one embodiment, sensor 212 includes a cardiac output or stroke volume sensor. Examples of stroke volume sensing are discussed in U.S. Pat. No. 4,686,987, "BIOMEDICAL METHOD AND APPARATUS FOR CONTROLLING THE ADMINISTRATION OF THERAPY TO A PATIENT IN RESPONSE TO CHANGES IN PHYSIOLOGIC DEMAND," and U.S. Pat. No. 5,284,136, "DUAL INDIFFERENT ELECTRODE PACEMAKER," both assigned to Cardiac Pacemakers, Inc., which are incorporated herein by reference in their entirety. Event detector 213 detects the abnormal condition when the stroke volume falls below a predetermined threshold level.

In one embodiment, sensor 212 includes a neural activity sensor to detect activities of the sympathetic nerve and/or the parasympathetic nerve. A significant decrease in cardiac output immediately stimulates sympathetic activities, as the autonomic nervous system attempts to compensate for deteriorated cardiac function. In one specific embodiment, the neural activity sensor includes a neurohormone sensor to sense a hormone level of the sympathetic nerve and/or the parasympathetic nerve. Event detector 213 detects the abnormal condition when the hormone level exceeds a predetermined threshold level. In another specific embodiment, the neural activity sensor includes an action potential recorder to sense the electrical activities in the sympathetic nerve and/or the parasympathetic nerve. Event detector 213 detects the abnormal condition when the frequency of the electrical activities in the sympathetic nerve exceeds a predetermined threshold level. Examples of direct and indirect neural activity sensing are discussed in U.S. Pat. No. 5,042,497, "ARRHYTHMIA PREDICTION AND PREVENTION FOR IMPLANTED DEVICES," assigned to Cardiac Pacemakers, Inc., which is hereby incorporated by reference in its entirety.

In one embodiment, sensor 212 includes a heart rate variability detector. Patients suffering acute decompensated heart failure exhibit abnormally low heart rate variability. An example of detecting the heart rate variability is discussed in U.S. Pat. No. 5,603,331, "DATA LOGGING SYSTEM FOR IMPLANTABLE CARDIAC DEVICE," assigned to Cardiac Pacemakers, Inc., which is incorporated herein by reference in their entirety. Event detector 213 detects the abnormal condition when the heart rate variability falls below a predetermined threshold level.

In one embodiment, sensor 212 includes a renal function sensor. Acute decompensated heart failure results in peripheral edema primarily because of fluid retention of the kidneys that follows the reduction in cardiac output. The fluid retention is associated with reduced renal output, decreased glomerular filtration, and formation of angiotensin. Thus, in one specific embodiment, the renal function sensor includes a renal output sensor to sense a signal indicative of the renal output. Event detector 213 detects the abnormal condition when the sensed renal output falls below a predetermined threshold. In another specific embodiment, the renal function sensor includes a filtration rate sensor to sense a signal indicative of the glomerular filtration rate. Event detector 213 detects the abnormal condition when the sensed glomerular filtration rate falls below a predetermined threshold. In yet another specific embodiment, the renal function sensor includes a chemical sensor to sense a signal indicative of angiotensin II levels. Event detector 213 detects the abnormal condition when the sensed angiotensin II levels exceed a predetermined threshold level.

In one embodiment, sensor 212 includes an acoustic sensor being a heart sound sensor and/or a respiratory sound sensor. Arrhythmias and/or heart failure cause abnormal cardiac and pulmonary activity patterns and hence, deviation of heart sounds and respiratory sounds from their normal ranges of pattern and/or amplitude. Event detector 213 detects the abnormal condition when the heart sound or respiratory sound is out of its normal range. For example, detection of the third heart sound (S3) is known to indicate heart failure. In one specific embodiment, event detector 213 detects the abnormal condition when the S3 amplitude or amount of S3 activity exceeds a predetermined threshold level. An example of using S3 activity to monitor for heart failure is discussed in U.S. patent application Ser. No. 10/746,874, "A THIRD HEART SOUND ACTIVITY INDEX FOR HEART FAILURE MONITORING," filed on Dec. 24, 2003, assigned to Cardiac Pacemakers, Inc., which is hereby incorporated by reference in its entirety.

Embodiments of sensor 212 and event detector 213 are discussed in this document by way of example, but not by way of limitation. In various embodiment, sensor 212 and event detector 213 may include combinations of various sensors and detectors discussed above. Other methods and sensors for directly or indirectly detecting an abnormal condition treatable by the gene regulatory therapy are generally useable by gene regulatory system 100.

In one specific embodiment, gene regulatory system 100 is used to treat heart failure. Sensor 212 includes a heart failure sensor sensing a signal indicative of heart failure. Examples of such a heart failure sensor include, but are not limited to, the impedance sensor, the pressure sensor, the cardiac output or stroke volume sensor, the neural activity sensor, the HRV sensor, the renal function sensor, and the acoustic sensor, which are discussed above. These sensors each sense a parameter indicative of heart failure or a symptom associated with heart failure, including acute decompensated heart failure. The heart failure sensor includes one or more of these sensors and any other sensors capable of sensing a signal and producing a parameter indicative of heart failure. In one embodiment, sensor 212 detects acute decompensated heart failure. Examples of detectors detecting acute decompensated heart failure are discussed in U.S. patent application Ser. No. 10/742,574, "DRUG DELIVERY SYSTEM AND METHOD EMPLOYING EXTERNAL DRUG DELIVERY DEVICE IN CONJUNCTION WITH COMPUTER NET- WORK," filed on Dec. 19, 2003, assigned to Cardiac Pacemakers, Inc., which is hereby incorporated by reference in its entirety.

Implantable CRM device 110A includes a hermetically sealed metal can to house at least portion of the electronics of the device. In one embodiment, sensor 212 resides within the metal can. In another embodiment, sensor 212 is outside of the metal can. In one embodiment, sensor 212 is incorporated into lead system 108. In one embodiment, sensor 212 is an external sensor communicating with implantable CRM device 110A. While implantable devices are specifically discussed as an example, the underlying concept can be implemented with either implantable medical devices, external (non-implantable) medical devices, or a combination of both.

Figure 3:
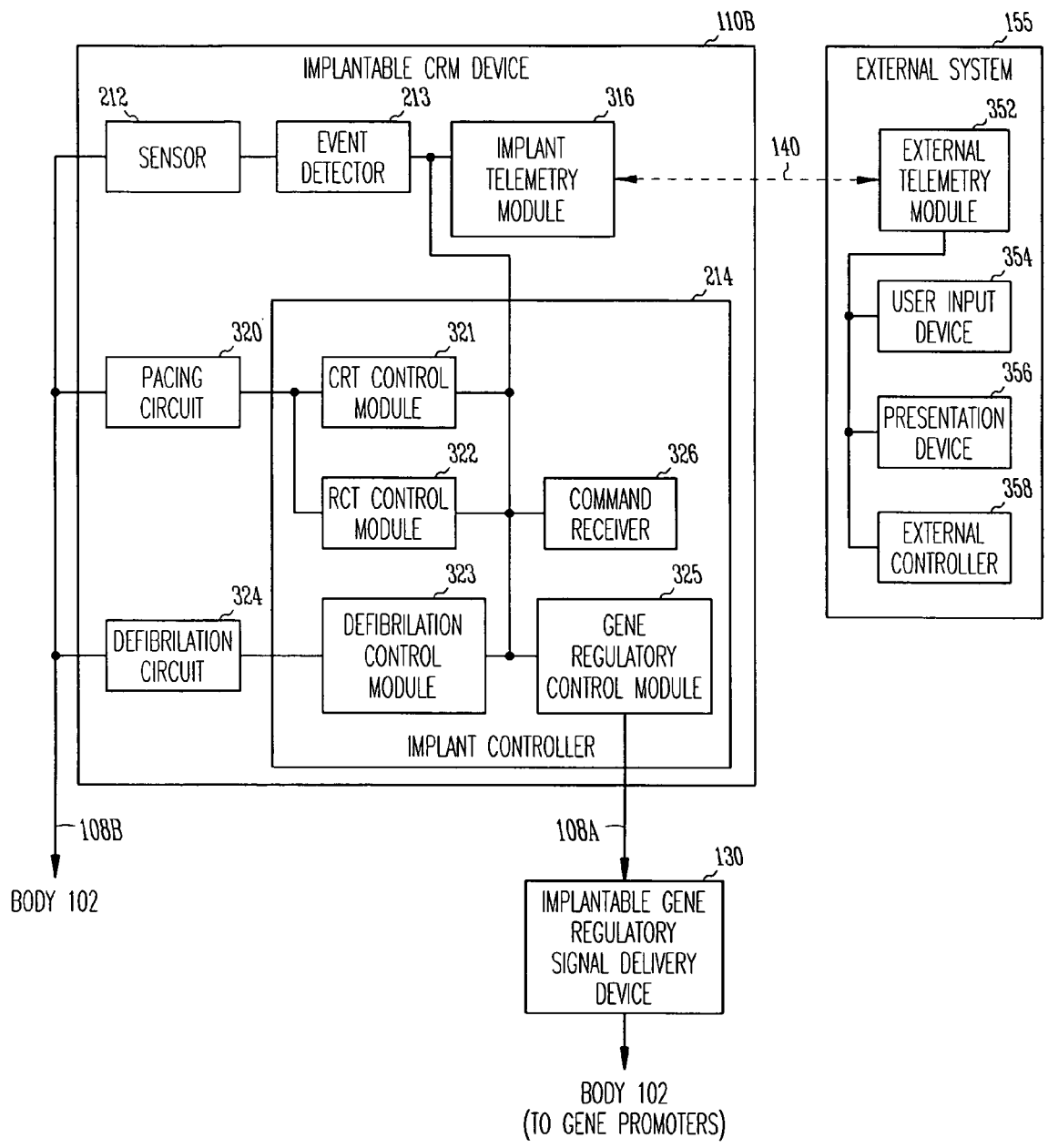
FIG. 3 is a block diagram showing another embodiment of the circuit of portions of the gene regulatory system such as shown in FIG. 1.

FIG. 3 is a block diagram showing another embodiment of the circuit of portions of system 100 including implantable CRM device 110A, lead system 108, implantable gene regulatory signal delivery device 130, and external system 155. Implantable CRM device 110B as shown in FIG. 3 represents one specific embodiment of implantable CRM device 110 and includes pacing and defibrillation capabilities. In addition to controlling the gene regulatory therapy, implantable CRM device 110B delivers therapies including, but not being limited to, bradyarrhythmia pacing, anti-tachyarrhythmia pacing, atrial and/or ventricular cardioversion/defibrillation, CRT, RCT, and drug delivery. However, such therapeutic capabilities are not necessary for system 100 to control the gene regulatory therapy, and hence, are not necessary elements of implantable CRM device 110B. In other words, implantable CRM device 110B can be an implantable pacemaker and/or defibrillator with additional functions including control of the gene regulatory therapy, or it can be a dedicated implantable gene regulatory therapy controller.

In one embodiment, implantable CRM device 110B includes sensor 212, event detector 213, implant controller 214, pacing circuit 320, defibrillation circuit 324, and implant telemetry module 316. Pacing circuit 320 delivers pacing pulses to one or more cardiac regions as controlled by implant controller 214. Defibrillation circuit 324 delivers cardioversion or defibrillation shocks to one or more cardiac regions as controlled by implant controller 214. Sensor 212 senses a physiological signal indicative of an abnormal condition treatable by the gene regulatory therapy, and event detector 213 detects that abnormal condition, as discussed above with reference to FIG. 2. In one specific embodiment, in which implantable CRM device provides for CRT and RCT pacing as well as defibrillation, implant controller 214 includes gene regulation control module 325, a CRT control module 321, an RCT control module 322, a defibrillation control module 323, and a command receiver 326. Gene regulation control module 325 generates the gene regulatory control signal in response to an abnormal condition detected by event detector 213 or a gene regulatory command received by command receiver 326. Command receiver 326 receives the gene regulatory command from external system 155 via telemetry link 140. CRT control module 321 controls the delivery of pacing pulses from pacing circuit 320 by executing a CRT algorithm. RCT control module 321 controls the delivery of pacing pulses from pacing circuit 320 by executing a RCT algorithm. Defibrillation control module 323 controls the delivery of cardioversion/defibrillation shocks from defibrillation circuit 324 when a tachyarrhythmic condition is detected. In one embodiment, defibrillation control module 323 includes an atrial defibrillation control module to control the delivery of cardioversion/defibrillation shocks to one or more of the atria. In one embodiment, defibrillation control module 323 includes a ventricular defibrillation control module to control the delivery of cardioversion/defibrillation shocks to one or more of the ventricles.

Implantable CRM device 110B includes a hermetically sealed metal can to house at least portion of the electronics of the device. In one embodiment, sensor 212 resides within the metal can. In another embodiment, sensor 212 is outside of the metal can. In one embodiment, sensor 212 is incorporated into lead system 108. In one embodiment, sensor 212 is an external sensor communicating with implantable CRM device 110B.

Lead system 108 includes one or more leads connecting implantable CRM device 110B and implantable gene regulatory signal delivery device 130, referenced as lead system 108A, and pacing leads, defibrillation leads, pacing-defibrillation leads, or any combination of such leads, referenced as lead system 108B. Lead system 108B allows sensing of electrical signals from various regions of heart 101 and/or delivery of pacing pulses and/or defibrillation shocks to various regions of heart 101. The various regions of heart 101 includes regions within or about the right atrium (RA), left atrium (LA), right ventricle (RV), and left ventricle (LV). In one embodiment, lead system 108B includes one or more transvenous leads each having at least one sensing-pacing or defibrillation electrode disposed within heart 101. In one embodiment, lead system 108B includes one or more epicardial leads each having at least one sensing-pacing or defibrillation electrode disposed on heart 101. In one embodiment, lead system 108B includes at least one atrial defibrillation electrode disposed in or about one or both of the atria to allow atrial defibrillation. In one embodiment, lead system 108B includes at least one ventricular defibrillation electrode disposed in or about one or both of the ventricles to allow ventricular defibrillation. In one embodiment, sensor 212 includes at least portions of lead system 108A or 108B. In another embodiment, sensor 212 is incorporated into lead system 108A or 108B.

External system 155 includes external telemetry module 352, external user input device 354, presentation device 356, and external controller 358. These system components distribute in one or more of external device 150, network 160, and remote device 170, depending on design and medical considerations. User input device 354 receives commands and/or parameters from the user and/or the patient to control deliveries of therapy, including the gene regulatory therapy, i.e., the delivery of the one or more gene regulatory signals. Presentation device 356 displays or otherwise presents signals acquired and/or abnormal conditions detected by implantable CRM device 110B. External controller 358 controls the operation of external system 155. In one embodiment, external controller 358 further provides automatic control of operations of implantable CRM device 110B. In one embodiment, user input device 352 receives the gene regulatory command entered by the user based on observations of the signals and/or abnormal conditions presented by presentation device 356. In another embodiment, user input device 352 receives the gene regulatory command entered by a patient when the patient physically senses a symptom indicative of an immediate need for the gene regulatory therapy, or entered by a person near the patient who observes a symptom indicative of the immediate need for the gene regulatory therapy. In a further embodiment, external controller 358 automatically analyzes the signals acquired and/or abnormal conditions detected by implantable CRM device 110B, and generates the gene regulatory command when deemed necessary as a result of the analysis.

Telemetry link 140 is a wireless bidirectional data transmission link supported by implant telemetry module 316 and external telemetry module 352. In one embodiment, telemetry link 140 is an inductive couple formed when two coils one connected to implant telemetry module 316 and the other connected to external telemetry module 352—are placed near each other. In another embodiment, telemetry link 140 is a far-field radio-frequency telemetry link allowing implantable CRM device 110B and external system 155 to communicate over a telemetry range that is at least ten feet.

Disorders Amenable to Treatment

The systems and methods of the invention may be used to prevent, inhibit or treat one or more symptoms of any condition amenable to treatment, prophylactic or otherwise, by gene therapy. In one embodiment, the systems of the invention are useful to treat, inhibit or prevent one or more symptoms of a cardiovascular condition. Cardiovascular conditions include but are not limited to coronary artery disease/ischemia, coronary artery disease (CAD), ischemia, angina (chest pain), thrombosis, coronary thrombosis, myocardial infarction (MI), silent ischemia, stenosis/restenosis, transient ischemic attack (TIA), atherosclerosis, peripheral vascular disease, bradyarrhythmia, e.g., bradyarrhythmia, bradycardia, sick sinus rhythm (Sick Sinus Syndrome), sinus bradycardia, sinoatrial block, asystole, sinus arrest, syncope, first degree atrio-ventricular (AV) block, second degree atrio-ventricular (AV) block, third degree atrio-ventricular (AV) block, chronotropic incompetence, tachyarrhythmia, e.g., tachyarrhythmia, tachycardia, fibrillation, flutter, atrial fibrillation, atrial flutter, familial atrial fibrillation, paroxysmal atrial fibrillation, permanent atrial fibrillation, persistent atrial fibrillation, supraventricular tachyarrhythmias, sinus tachycardia, reentry (reentrant arrhythmias), AV nodal reentry, focal arrhythmia, ectopy, ventricular fibrillation (VF), ventricular tachycardia (VT), Wolff-Parkinson-White Syndrome (WPW) and sudden cardiac death, heart failure, e.g., heart failure, cardiomyopathy, congestive heart failure, hypertrophic cardiomyopathy, remodeling, non-ischemic cardiomyopathy, dilated cardiomyopathy, restrictive cardiomyopathy, diastolic heart failure, systolic heart failure, and chronic heart failure, heart block/electrical disorders, e.g., atrioventricular (AV) block, bundle branch block (BBB), left bundle branch block (LBBB), right bundle branch block (RBBB), Long QT Syndrome (LQTS), premature ventricular contraction (PVC), electrical remodeling, intraventricular conduction defect, and hemiblock, hemodynamic deficiency, e.g., hypertension, hypotension, left ventricular dysfunction, low ejection fraction, low cardiac output, and low stroke volume, sudden cardiac death, cardiac arrest, sudden cardiac death (SCD), ventricular fibrillation, and pump failure, as well as bacterial endocarditis, viral myocarditis, pericarditis, rheumatic heart disease, and syncope. In particular, a cardiovascular condition includes, but is not limited to, arrhythmia, e.g., atrial fibrillation, ventricular fibrillation or bradycardia, ischemia, heart failure and hyperplasia not associated with neoplastic disease, which may be associated with ventricular remodeling, diastolic dysfunction, aberrant body temperature, aberrant or altered pressure, e.g., altered venous, left ventricular or left atrial pressure, aberrant or altered heart rate or sounds, aberrant or altered electrogram, aberrant or altered cardiac metabolism, such as altered blood pH, glucose, $PO_2$, $PCO_2$, minute ventilation, creatine, CRP, Mef2A, creatine kinase or creatine kinase MB levels, aberrant or altered pulmonary or thoracic impedence, aberrant or altered stroke volume, aberrant or altered neurohormone levels, aberrant or altered electrical activity, aberrant or altered sympathetic nerve activity, aberrant or altered renal output, aberrant or altered filtration rate, aberrant or altered angiotensin II levels, or aberrant or altered respiratory sounds.

For instance, cardiovascular conditions associated with certain defective genes (see Table 1), e.g., disease alleles, may be treated by gene therapy.

TABLE 1

| Condition | Current | Defective gene |
|---|---|---|
| LQT-1 | $I_{KS}$ amplitude | KVLQTI(KCNQ1) |
| LQT-2 | $I_{Kr}$ amplitude | HERG (KCNH2) |
| LQT-3 | $I_{Na}$ late current | SCN5a (hNaV$_{1.5}$) |
| LQT-5 | $I_{KS}$ amplitude | MinK (KCNE1) |
| LQT-6 | $I_{Kr}$ deactivation | MiRPI (KCNE2) |
| LQT-7 | $I_{KI}$ amplitude | Kir2.1 (KCNj2) |
| JLN-1 | $I_{KS}$ amplitude | KVLQTI(KCNQ1) |
| JLN-2 | $I_{Kr}$ amplitude | MinK(KCNEI) |
| SIDS-1 | $I_{Na}$ late current | SCN5a(hNaV$_{1.5}$) |
| SIDS-2 | $I_{KS}$ amplitude | KVLQTI(KCNQ1) |
| Brugada syndrome | $I_{Na}$ amplitude | SCN5a(hNaV$_{1.5}$) |
| IVF | $I_{Na}$ amplitude | SCN5a(hNaV$_{1.5}$) |
| CVT | Cell $Ca^{2+}$ | RyR receptor |
| CCD | $I_{Na}$ amplitude | SCN5a(hNaV$_{1.5}$) |

JLN = Jerrell & Lange-Nielsen;
SIDS = sudden infant death syndrome;
IVF = idiopathic ventricular fibrillation;
CVT = catecholaminergic ventricular tachycardia;
CCD = cardiac conduction disease Gene Therapy Vectors Gene therapy vectors include, for example, viral vectors, liposomes and other lipid-containing complexes, and other macromolecular complexes capable of mediating delivery of a gene to a host cell. Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector by the cell; components that influence localization of the transferred gene within the cell after uptake (such as agents mediating nuclear localization); and components that influence expression of the gene. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., WO 92/08796; and WO 94/28143). Such marker genes can provide an added measure of control that can be advantageous in gene therapy contexts. A large variety of such vectors are known in the art and are generally available.

Gene therapy vectors within the scope of the invention include, but are not limited to, isolated nucleic acid, e.g., plasmid-based vectors which may be extrachromosomally maintained, and viral vectors, e.g., recombinant adenovirus, retrovirus, lentivirus, herpesvirus, poxvirus, papilloma virus, or adeno-associated virus, including viral and non-viral vectors which are present in liposomes, e.g., neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes. Exemplary gene therapy vectors are described below. Gene therapy vectors may be administered via any route including, but not limited to, intramuscular, buccal, rectal, intravenous or intracoronary administration, and transfer to cells may be enhanced using electroporation and/or iontophoresis.

Retroviral Vectors

Retroviral vectors exhibit several distinctive features including their ability to stably and precisely integrate into the host genome providing long-term transgene expression. These vectors can be manipulated ex vivo to eliminate infectious gene particles to minimize the risk of systemic infection and patient-to-patient transmission. Pseudotyped retroviral vectors can alter host cell tropism.

Lentiviruses

Lentiviruses are derived from a family of retroviruses that include human immunodeficiency virus and feline immunodeficiency virus. However, unlike retroviruses that only infect dividing cells, lentiviruses can infect both dividing and non-dividing cells. For instance, lentiviral vectors based on human immunodeficiency virus genome are capable of efficient transduction of cardiac myocytes in vivo. Although lentiviruses have specific tropisms, pseudotyping the viral envelope with vesicular stomatitis virus yields virus with a broader range (Schnepp et al., *Meth. Mol. Med.*, 69:427 (2002)).

Adenoviral Vectors

Adenoviral vectors may be rendered replication-incompetent by deleting the early (E1A and E1B) genes responsible for viral gene expression from the genome and are stably maintained into the host cells in an extrachromosomal form. These vectors have the ability to transfect both replicating and nonreplicating cells and, in particular, these vectors have been shown to efficiently infect cardiac myocytes in vivo, e.g., after direction injection or perfusion. Adenoviral vectors have been shown to result in transient expression of therapeutic genes in vivo, peaking at 7 days and lasting approximately 4 weeks. The duration of transgene expression may be improved in systems utilizing cardiac specific promoters. In addition, adenoviral vectors can be produced at very high titers, allowing efficient gene transfer with small volumes of virus.

Adeno-Associated Virus Vectors

Recombinant adeno-associated viruses (rAAV) are derived from nonpathogenic parvoviruses, evoke essentially no cellular immune response, and produce transgene expression lasting months in most systems. Moreover, like adenovirus, adeno-associated virus vectors also have the capability to infect replicating and nonreplicating cells and are believed to be nonpathogenic to humans. Moreover, they appear promising for sustained cardiac gene transfer (Hoshijima et al., *Nat. Med.*, 8:864 (2002); Lynch et al., *Circ. Res.*, 80:197 (1997)).

Herpesvirus/Amplicon

Herpes simplex virus 1 (HSV-1) has a number of important characteristics that make it an important gene delivery vector in vivo. There are two types of HSV-1-based vectors: 1) those produced by inserting the exogenous genes into a backbone virus genome, and 2) HSV amplicon virions that are produced by inserting the exogenous gene into an amplicon plasmid that is subsequently replicated and then packaged into virion particles. HSV-1 can infect a wide variety of cells, both dividing and nondividing, but has obviously strong tropism towards nerve cells. It has a very large genome size and can accommodate very large transgenes (>35 kb). Herpesvirus vectors are particulary useful for delivery of large genes, e.g., genes encoding ryanodine receptors and titin.

Plasmid DNA Vectors

Plasmid DNA is often referred to as "naked DNA" to indicate the absence of a more elaborate packaging system. Direct injection of plasmid DNA to myocardial cells in vivo has been accomplished. Plasmid-based vectors are relatively nonimmunogenic and nonpathogenic, with the potential to stably integrate in the cellular genome, resulting in long-term gene expression in postmitotic cells in vivo. For example, expression of secreted angiogenesis factors after muscle injection of plasmid DNA, despite relatively low levels of focal transgene expression, has demonstrated significant biologic effects in animal models and appears promising clinically (Isner, *Nature,* 415:234 (2002)). Furthermore, plasmid DNA is rapidly degraded in the blood stream; therefore, the chance of transgene expression in distant organ systems is negligible. Plasmid DNA may be delivered to cells as part of a macromolecular complex, e.g., a liposome or DNA-protein complex, and delivery may be enhanced using techniques including electroporation.

Synthetic Oligonucleotides

Antisense oligonucleotides are short (approximately 10 to 30 nucleotides in length), chemically synthesized DNA molecules that are designed to be complementary to the coding sequence of an RNA of interest. These agents may enter cells by diffusion or liposome-mediated transfer and possess relatively high transduction efficiency. These agents are useful to reduce or ablate the expression of a targeted gene while unmodified oligonucleotides have a short half-life in vivo, modified bases, sugars or phosphate groups can increase the half-life of oligonucleotide. For unmodified nucleotides, the efficacy of using such sequences is increased by linking the antisense segment with a specific promoter of interest, e.g., in an adenoviral construct. In one embodiment, electroporation and/or liposomes are employed to deliver plasmid vectors. Synthetic oligonucleotides may be delivered to cells as part of a macromolecular complex, e.g., a liposome, and delivery may be enhanced using techniques such as electroporation.

Regulatable Transcriptional Control Elements

The device of the invention may deliver one or more signals including, but not limited to, light of a particular wavelength or a range of wavelengths, light of a particular energy, acoustic energy, an electric field, a chemical, electromagnetic energy, thermal energy or other forms of temperature or matter, which signal is recognized by a regulatable transcriptional control element in a gene therapy vector.

A variety of strategies have been devised to control in vivo expression of transferred genes and thus alter the pharmacokinetics of in vivo gene transfer vectors in the context of regulatable or inducible promoters. Many of these regulatable promoters use exogenously administered agents to control transgene expression and some use the physiologic milieu to control gene expression. Examples of the exogenous control promoters include the tetracycline-responsive promoter, a chimeric transactivator consisting of the DNA and tetracycline-binding domains from the bacterial tet repressor fused to the transactivation domain of herpes simplex virion protein 16 (Ho et al., *Brain Res. Mol. Brain Res.*, 41:200 (1996)); a chimeric promoter with multiple cyclic adenosine monophosphate response elements superimposed on a minimal fragment of the 5'-flanking region of the cystic fibrosis transmembrane conductance regulator gene (Suzuki et al., 7:1883

(1996)); the EGR1 radiation-inducible promoter (Hallahan et al., *Nat. Med.,* 1:786 (1995)); and the chimeric GRE promoter (Lee et al., *J. Thoracic Cardio. Surg.,* 118:26 (1996)), with 5 GREs from the rat tyrosine aminotransferase gene in tandem with the insertion of Ad2 major late promoter TATA box-initiation site (Narumi et al., *Blood,* 92:812 (1998)). Examples of the physiologic control of promoters include a chimera of the thymidine kinase promoter and the thyroid hormone and retinoic acid-responsive element responsive to both exogenous and endogenous tri-iodothyroniine (Hayashi et al., *J. Biol. Chem.,* 269:23872 (1994)); complement factor 3 and serum amyloid A3 promoters responsive to inflammatory stimuli; the grp78 and BiP stress-inducible promoter, a glucose-regulated protein that is inducible through glucose deprivation, chronic anoxia, and acidic pH (Gazit et al., *Cancer Res.,* 55:1660 (1995)); and hypoxia-inducible factor 1 and a heterodimeric basic helix-loop-helix protein that activates transcription of the human erythropoietin gene in hypoxic cells, which has been shown to act as a regulatable promoter in the context of gene therapy in vivo (Forsythe et al., *Mol. Cell Biol.,* 16:4604 (1996)).

Regulatable transcriptional elements useful in gene therapy vectors and methods of the invention include, but are not limited to, a truncated ligand binding domain of a progesterin receptor (controlled by antiprogestin), a tet promoter (controlled by tet and dox) (Dhawan et al., *Somat. Cell. Mol. Genet.,* 21, 233 (1995); Gossen et al., *Science,* 268:1766 (1995); Gossen et al., *Science,* 89:5547 (1992); Shockett et al., *Proc. Natl. Acad. Sci. USA,* 92, 6522 (1995)), hypoxia-inducible nuclear factors (Semenza et al., *Proc. Natl. Acad. Sci. USA,* 88, 5680 (1991); Semenza et al., *J. Biol. Chem.,* 269, 23757)), steroid-inducible elements and promoters, such as the glucocorticoid response element (GRE) (Mader and White, *Proc. Natl. Acad. Sci. USA,* 90, 5603 (1993)), and the fusion consensus element for RU486 induction (Wang et al., *Proc. Natl. Acad. Sci. USA,* 91:818 (1994)), those sensitive to electromagnetic fields, e.g., those present in metallothionein I or II, c-myc, and HSP70 promoters (Lin et al., *J. Cell. Biochem.,* 81:143 (2001); Lin et al., *J. Cell. Biochem.,* 54:281 (1994); U.S. published application 20020099026)), and electric pulses (Rubenstrunk et al., *J. Gene Med.,* 5:773 (2003)), as well as a yeast GAL4/TATA promoter, auxin inducible element, an ecdysone responsive element (No et al., *Proc. Natl. Acad. Sci. USA,* 93:3346 (1996)), an element inducible by rapamycin (FK506) or an analog thereof (Rivera et al., *Nat. Med.,* 2:1028 (1996); Ye et al., *Science,* 283:88 (1999); Rivera et al., *Proc. Natl. Acad. Sci. USA,* 96:8657 (1999)), a tat responsive element, a metal, e.g., zinc, inducible element, a radiation inducible element, e.g., ionizing radiation has been used as the inducer of the promoter of the early growth response gene (Erg-1) (Hallahan et al., *Nat. Med.,* 1:786 (1995)), an element which binds nuclear receptor PPARγ (peroxisome proliferators activated receptors), which is composed of a minimal promoter fused to PPRE (PPAR responsive elements, see WO 00/78986), a cytochrome P450/A1 promoter, a MDR-1 promoter, a promoter induced by specific cytokines (Varley et al., *Nat. Biotech.,* 15:1002 (1997)), a light inducible element (Shimizu-Sato et al., *Nat. Biotech.,* 20:1041 (2002)), a lacZ promoter, and a yeast Leu3 promoter.

In some embodiments, cell- or tissue-specific control elements, such as muscle-specific and inducible promoters, enhancers and the like, will be of particular use, e.g., in conjunction with regulatable transcriptional control elements. Such control elements include, but are not limited to, those derived from the actin and myosin gene families, such as from the myoD gene family (Weintraub et al., *Science,* 251, 761 (1991)); the myocyte-specific enhancer binding factor MEF-2 (Cserjesi and Olson, *Mol. Cell Biol.,* 11, 4854 (1991)); control elements derived from the human skeletal actin gene (Muscat et al., *Mol. Cell Bio.,* 7, 4089 (1987)) and the cardiac actin gene; muscle creatine kinase sequence elements (Johnson et al., *Mol. Cell Biol.,* 9, 3393 (1989)) and the murine creatine kinase enhancer (mCK) element; control elements derived from the skeletal fast-twitch troponin C gene, the slow-twitch cardiac troponin C gene and the slow-twitch troponin I genes.

Cardiac cell restricted promoters include but are not limited to promoters from the following genes: a α-myosin heavy chain gene, e.g., a ventricular α-myosin heavy chain gene, P-myosin heavy chain gene, e.g., a ventricular β-myosin heavy chain gene, myosin light chain 2v gene, e.g., a ventricular myosin light chain 2 gene, myosin light chain 2a gene, e.g., a ventricular myosin light chain 2 gene, cardiomyocyte-restricted cardiac ankyrin repeat protein (CARP) gene, cardiac α-actin gene, cardiac m2 muscarinic acetylcholine gene, ANP gene, BNP gene, cardiac troponin C gene, cardiac troponin I gene, cardiac troponin T gene, cardiac sarcoplasmic reticulum Ca-ATPase gene, skeletal α-actin gene, as well as an artificial cardiac cell-specific promoter.

Further, chamber-specific promoters or enhancers may also be employed, e.g., for atrial-specific expression, the quail slow myosin chain type 3 (MyHC3) or ANP promoter, or the cGATA-6 enhancer, may be employed. For ventricle-specific expression, the iroquois homeobox gene may be employed. Examples of ventricular myocyte-specific promoters include a ventricular myosin light chain 2 promoter and a ventricular myosin heavy chain promoter.

In other embodiments, disease-specific control elements may be employed. Thus, control elements from genes associated with a particular disease, including but not limited to any of the genes disclosed herein may be employed in vectors of the invention.

Nevertheless, other promoters and/or enhancers which are not specific for cardiac cells or muscle cells, e.g., RSV promoter, may be employed in the expression cassettes and methods of the invention. Other sources for promoters and/or enhancers are promoters and enhancers from the Csx/NKX 2.5 gene, titin gene, α-actinin gene, myomesin gene, M protein gene, cardiac troponin T gene, RyR2 gene, Cx40 gene, and Cx43 gene, as well as genes which bind Mef2, dHAND, GATA, CarG, E-box, Csx/NKX 2.5, or TGF-beta, or a combination thereof.

The response of the regulatable transcriptional control element to one or more intermittent signals, a prolonged signal or different levels of a signal, may be tested in vitro or in vivo. The vector may include the regulatable transcriptional control element linked to a marker gene, i.e., one which is readily detectable or capable of detection such as green fluorescent protein (GFP). For example, a vector having a promoter which is sensitive to electrical pulses, a MT-I or MT-II promoter (Rubenstruck et al., *J. Gene Med.,* 5:773 (2003)), is linked to an open reading frame for a marker gene. The resulting expression cassette, e.g., one which is introduced to an adenovirus vector or to a plasmid vector, is employed to infect or transfect murine cells, e.g., murine cardiac cells, or heart sections. An electrode system designed for use in a small flask is used to deliver electrical pulses. Then fluorescence in the cells or a lysate thereof is detected, and/or or vector specific RNA is measured, for instance, using RT-PCR, and optionally compared to data from control cells. Similarly, a vector having a promoter which is sensitive to electrical pulses is linked to an open reading frame for a therapeutic gene, e.g., Serca2, introduced to cells, e.g., cardiac cells such as those with decreased levels of the gene product encoded by the therapeutic gene, and the phenotype of the recombinant cells compared to control cells. Vectors may also be introduced to a non-human large animal model, e.g., pigs, to determine the level and spatial expression of the exogenously introduced gene in response to signals, e.g., electrical pulses, from an implantable device in that animal.

Exemplary Genes for Gene Therapy Vectors

Open reading frames useful in gene therapy vectors include those for hepatocyte growth factor, $ARK_{Ct}$, endothelial GF121, angiotensin type II receptor, p16INK4a, heat shock protein (HSP), e.g., HSP70, sodium channel protein, e.g., SCN5A, C reactive protein, connexin, e.g., connexin 40, 41, 43 or 45, sarcoplasmic reticulum $Ca^{2+}$ ATPase (SERCA2a), ryanodine receptor, MiRPI, cardiac endothelin-1, KCNEI ($I_{Ks}$), protein kinase C, HIF-1α, p38MAPK, Cox-2, phospholamban, matrix metalloproteinases, adrenergic receptors (AR) and kinases therefore, e.g., betaAR and betaARK, adenylylcyclase, cytochrome oxidase B subunit III, ATP synthase subunit 6, calcium channel proteins such as voltage gated $Ca^{2+}$ channels, potassium channel proteins such as KCNA5(Kv1.5), KCND2(Kv4.2), KCND3 (Kv 4.3, $I_{to}$), KCNEI (minK), KCNE2, KCNQ1, as well as K+ inwardly rectifying channel such as Kir3.1 (KCNJ3), KCNH2 (HERG, $I_{kr}$), Kv4.3, Kir3.4, Kir6.1 and Kir6.2, and open reading frames for the sodium-calcium exchanger ($I_{Na/Ca}$), e.g., NCKX1-4. Examples of preferred βAR include $β_1$-adrenergic receptors or $β_2$-adrenergic receptors, and preferred adenylylcyclases include a cardiac AC such as $AC_V$ or $AC_{V1}$, more preferably $AC_{V1}$. See also Tables 1 and 2 for genes useful in cardiovascular applications.

TABLE 2

| Subunit | Corresponding Current | Primary Function |
|---|---|---|
| HCN | $I_f$ (pacemaking) | Diastolic depolarization |
| Kir 2.1 | $I_{kl}$ | Resting potential, terminal repolarization |
| Kir3.1/3.4 | $I_{KACh}$ | Mediates acetylcholine effects |
| ERG | $I_{Kr}$ (α-subunit) | Phase-3 repolarization |
| MiRP1 | Modulates $I_{Kr}, I_f, I_{to}$ | |
| KvLQT1 | $I_{Ks}$ (α-subunit) | Phase-3 repolarization (esp. with β-adrenergic stimulation, $I_{Kr}$ inhibition) |
| mink | $I_{Ks}$ (β-subunit) | Necessary to form $I_{Ks}$ with KvLQT1. |
| Kv4.2/4.3 | $I_{to}$ (α-subunit) | Early (phase-1) repolarization |
| Kv1.4 | $I_{to}$ (α-subunit) | Early (phase-1) repolarization |
| KChIP2 | $I_{to}$ (β-subunit) | Necessary to form $I_{to}$ |
| Kv1.5/3.1 | $I_{Kur}$ | Phase 1–2 repolarization |
| $Ca_v 1.2$ | $I_{CaL}$ (α-subunit) | Maintenance of plateau. Electromechanical coupling. Automaticity, conduction SAN, AVN |
| $Ca_v 1.3$ | $I_{CaL}$ component | Role in SAN function in mice. |
| $Ca_v 3, 103, 3$ | $I_{CaT}$ | Role in pacemaking |
| $Na_v 1.5$ | $I_{Na}$ | Conduction A, V, PF |
| Cx40, 43, 45 | $I_{GJ}$ | Intercellular conduction |

Other genes of interest encode angiogens, acidic fibroblast growth factor (aFGF), basic fibroblast growth factor (bFGF), fibroblast growth factor 3 (FGF-3), fibroblast growth factor 4 (FGF-4), fibroblast growth factor 5 (FGF-5), fibroblast growth factor 6 (FGF-6), fibroblast growth factor 7 (FGF-7), fibroblast growth factor 8 (FGF-8), fibroblast growth factor 9 (FGF-9), angiogenin 1, angiogenin 2, platelet-derived endothelial-cell growth factor (PD-ECGF), transforming growth factor-α (TGF-α), transforming growth factor-β (TGF-β), tumor necrosis factor-α (TNF-α), vascular endothelial growth factor 121 (VEGF 121), vascular endothelial growth factor 165 (VEGF 165), vascular endothelial growth factor 189 (VEGF 189), vascular endothelial growth factor 206 (VEGF 206), vascular endothelial growth factor B (VEGF-B), vascular endothelial growth factor C (VEGF-C), vascular endothelial growth factor D (VEGF-D), vascular endothelial growth factor E (VEGF-E), vascular endothelial growth factor F (VEGF-F), angiopoietin-1, angiopoietin-2, thrombospondin (TSP), proliferin, ephrin-A1 (B61), e-selectin, chicken chemotactic and angiogenic factor (cCAF), leptin, heparin affin regulatory peptide (HARP), platelet derived growth factor (PDGF), e.g., PDGF-AA, PDGF-AB or PDGF-BB, or heparin.

Thus, in one embodiment, the transgene encodes a gene product including but not limited to an angiogenic protein, e.g., a fibroblast growth factor (FGF) such as acidic-FGF, basic-FGF, and FGF-5, vascular endothelial growth factor (VEGF), e.g., $VEGF_{145}$, $VEGF_{121}$, $VEGF_{120}$, $VEGF_{164}$, $VEGF_{165}$, $VEGF_{189}$, and $VEGF_{206}$, IGF-1, TGF-beta, e.g., $TGF-beta_1$, leukemia inhibitory factor (LIF) alone or in combination with other cytokines, a myogenic factor, e.g., myoD, RyR (cardiac ryanodine receptor), Del I, myogenin, parvalbumin, Myf5, and MRF, transcription factors (GATA such as GATA-4 and dHAND/eHAND), cytokines such as cardiotrophin-1, calsequestrin, neuregulin, for instance, neuregulin 1, 2 or 3, and homeobox gene products, e.g., Csx, tinman, and the NKx family, e.g., NKx 2.5, transferrin, platelet-derived growth factor (PDGF), epidermal growth factor (EGF), adrenocorticotrophin, macrophage colony-stimulating factor, protein kinase C activators, endothelial growth factor, β2 adrenergic receptor (1 or 2), mutant G protein receptor kinase (GRK), adenylyl cylase (AC), e.g., cardiac AC such as human type II, V or VI adenyl cylase (U.S. Pat. No. 6,436,672), V2 vasopressin receptor, phospholambam, β-adrenergic receptor kinase, N-cadherin, connexin-40, connexin-42, connexin-43, contractable proteins, e.g., myosin heavy chain (MyHC), myosin light chain (MyLC), myosin binding protein C, actin, tropomyosin, troponin, e.g., troponin T, M protein, tropomodulin, myofibrillar protein, stress related protein, e.g., HSP such as HSP70i, HSP27, HSP40 or HSP60, α-1 antitrypsin, HF1-α, HF-1b, MEF2, BMP-2, BMP-4, BMP-17, BMP-18, Pax7, oxytocin, oxytocin receptor, myocyte nuclear factor, Frzb (see published U.S. application 20020147329), Rb-interacting zinc finger protein (U.S. Pat. No. 6,468,985), nNOS, eNOS, iNOS, serine/threonine protein phosphatase, cardiac hypertrophy factor, CT-1, α, β, γ or δ sarcoglycan, hypoxia inducible factor 1α, bcl-2, FasL, cytokine gp 130 receptor, gp130, Akt, adenosine A3 receptor, angiogenin, e.g., angiogenin-1 or angiogenin-2, TNFα, dystrophin, tafazzin, desmin, lamin, troponin C, caspase inhibitors, ERK-type of MAP kinases (p42 and p44, anti-apoptosis), IL-1B, serum releasing factor, and ILGF (I and II), NGF, growth hormone, e.g., human growth hormone, or angiotensin, e.g., angiotensin II.

In another embodiment, e.g., for cells from a mammal with an inherited or acquired disorder such as one characterized by overexpression of certain endogenous genes (wild type or mutant), the transgene may comprise antisense or ribozyme sequences which substantially correspond to the reverse complement of at least a portion of the endogenous gene, and which antisense or ribozyme sequence, when expressed in a cell of a mammal with the disorder, results in a decrease in the expression of the endogenous gene. Alternatively, the transgene may comprise sequences which, after homologous recombination with the endogenous gene, e.g., a disease allele, result in a decrease in the expression of the endogenous gene and increased expression of the transgene.

Vector or Recombinant Cell Delivery

Several techniques have been developed for cardiac gene delivery, including pericardial infusion, endomyocarial injection, intracoronary injection, coronary venous retroperfusion, and aortic root injection (Isner, *Nature,* 415:234 (2002)). The different techniques achieve variable response in homogeneity of gene delivery, resulting in focal gene expression within the heart (Hajjar et al., *Circ. Res.,* 86:616 (2000). For this reason, techniques that achieve diffuse uptake would seem to be superior. Two such methods utilize the heart's arterial and venous circulation to accomplish disseminated viral transfection. Arterial injection, performed directly through a percutaneous approach or indirectly by an infusion into the cross-clamped aorta, has shown promise in animal models of heart failure and is appealing in that it can be performed either at the time of cardiac surgery or as percutaneous intervention (Hajjar et al., *PNAS USA,* 95:5251 (1998)). Similarly, retroperfusion through the coronary sinus appears to produce a more global gene expression in comparison with techniques of localized or focal injection (Boeckstegers et al., *Circ.,* 100:1 (1999)).

Recombinant cells may be administered intravenously, transvenously, intramyocardially or by any other convenient route, and delivered by a needle, catheter, e.g., a catheter which includes an injection needle or infusion port, or other suitable device.

Direct Myocardial Injection

Direct myocardial injection of plasmid DNA as well as virus vectors, e.g., adenoviral vectors, and cells including recombinant cells has been documented in a number of in vivo studies. This technique when employed with plasmid DNA or adenoviral vectors has been shown to result in effective transduction of cardiac myocytes. Thus, direct injection may be employed as an adjunct therapy in patients undergoing open-heart surgery or as a stand-alone procedure via a modified thorascope through a small incision. In one embodiment, this mode of administration is used to deliver a gene or gene product that would only require limited transfection efficiency to produce a significant therapeutic response, such as a gene that encodes for or leads to a secreted product (e.g., VEGF, endothelial nitric oxide synthase). Virus, e.g., pseudotyped, or DNA- or virus-liposome complexes may be delivered intramyocardially.

Catheter-Based Delivery

Intracoronary delivery of genetic material can result in transduction of approximately 30% of the myocytes predominantly in the distribution of the coronary artery. Parameters influencing the delivery of vectors via intracoronary perfusion and enhancing the proportion of myocardium transduced include a high coronary flow rate, longer exposure time, vector concentration, and temperature. Gene delivery to a substantially greater percent of the myocardium may be enhanced by administering the gene in a low-calcium, high-serotonin mixture (Donahue et al., *Nat. Med.,* 6:1395 (2000)). The potential use of this approach for gene therapy for heart failure may be increased by the use of specific proteins that enhance myocardial uptake of vectors (e.g., cardiac troponin T).

Improved methods of catheter-based gene delivery have been able to achieve almost complete transfection of the myocardium in vivo. Hajjar et al. (*Proc. Natl. Acad. Sci. USA,* 95:5251 (1998)) used a technique combining surgical catheter insertion through the left ventricular apex and across the aortic valve with perfusion of the gene of interest during cross-clamping of the aorta and pulmonary artery. This technique resulted in almost complete transduction of the heart and could serve as a protocol for the delivery of adjunctive gene therapy during open-heart surgery when the aorta can be cross-clamped.

Recombinant cells may also be delivered via catheter.

Pericardial Delivery

Gene delivery to the ventricular myocardium by injection of genetic material into the pericardium has shown efficient gene delivery to the epicardial layers of the myocardium. However, hyaluronidase and collagenase may enhance transduction without any detrimental effects on ventricular function. Recombinant cells may also be delivered pericardially.

Intravenous Delivery

Intravenous gene delivery may be efficacious for myocardial gene delivery. However, to improve targeted delivery and transduction efficiency of intravenously administered vectors, targeted vectors may be employed. In one embodiment, intravenous administration of DNA-liposome or antibody-DNA complexes may be employed.

Lead-Based Delivery

Gene delivery can be performed by incorporating a gene delivery device or lumen into a lead such as a pacing lead, defibrillation lead, or pacing-defibrillation lead. An endocardial lead including a gene delivery device or lumen allows gene delivery to the endocardial layers of the myocardium. An epicardial lead including a gene delivery device or lumen allows gene delivery to the endocardial layers of the myocardium. A transvenous lead including a gene delivery device or lumen may also allow intravenous gene delivery. Lead-based delivery is particularly advantageous when the lead is used to deliver electrical and gene therapies to the same region.

Generally any route of administration may be employed, including oral, mucosal, intramuscular, buccal and rectal administration. For certain vectors, certain route of administration may be preferred. For instance, viruses, e.g., pseudotypsed virus, and DNA- or virus-liposome, e.g., HVJ-liposome, may be administered by coronary infusion, while HVJ-liposome complexes may be delivered pericardially.

Recombinant cells may also be delivered systemically, e.g., intravenously.

Targeted Vectors

The present invention contemplates the use of cell targeting not only by delivery of the transgene or recombinant cell into the coronary artery, for example, but also by use of targeted vector constructs having features that tend to target gene delivery and/or gene expression to particular host cells or host cell types (such as the myocardium). Such targeted vector constructs would thus include targeted delivery vectors and/or targeted vectors, as described herein. Restricting delivery and/or expression can be beneficial as a means of further focusing the potential effects of gene therapy. The potential usefulness of further restricting delivery/expression depends in large part on the type of vector being used and the method and place of introduction of such vector. For instance, delivery of viral vectors via intracoronary injection to the myocardium has been observed to provide, in itself, highly targeted gene delivery. In addition, using vectors that do not result in transgene integration into a replicon of the host cell (such as adenovirus and numerous other vectors), cardiac myocytes are expected to exhibit relatively long transgene expression since the cells do not undergo rapid turnover. In contrast, expression in more rapidly dividing cells would tend to be decreased by cell division and turnover. However, other means of limiting delivery and/or expression can also be employed, in addition to or in place of the illustrated delivery method, as described herein.

Targeted delivery vectors include, for example, vectors (such as viruses, non-viral protein-based vectors and lipid-based vectors) having surface components (such as a member of a ligand-receptor pair, the other half of which is found on a host cell to be targeted) or other features that mediate preferential binding and/or gene delivery to particular host cells or host cell types. As is known in the art, a number of vectors of both viral and non-viral origin have inherent properties facilitating such preferential binding and/or have been modified to effect preferential targeting (see, e.g., Miller, et al., *FASEB Journal*, 9:190 (1995); Chonn et al., *Curr. Opin. Biotech.*, 6:698 (1995); Schofield et al., *British Med. Bull.*, 51:56 (1995); Schreier, *Pharmaceutica Acta Helvetiae*, 68:145 (1994); Ledley, *Human Gene Therapy*, 6:1129 (1995); WO 95/34647; WO 95/28494; and WO 96/00295).

Targeted vectors include vectors (such as viruses, non-viral protein-based vectors and lipid-based vectors) in which delivery results in transgene expression that is relatively limited to particular host cells or host cell types. For example, transgenes can be operably linked to heterologous tissue-specific enhancers or promoters thereby restricting expression to cells in that particular tissue. For example, tissue-specific transcriptional control sequences derived from a gene encoding left ventricular myosin light chain-2 ($MLC_2V$) or myosin heavy chain (MHC) can be fused to a transgene within a vector. Expression of the transgene can therefore be relatively restricted to ventricular cardiac myocytes.

Dosages and Dosage Forms

The amount of gene therapy vector(s), e.g., those which are present in a recombinant cell or in acellular form, administered and device based signal emitted to achieve a particular outcome will vary depending on various factors including, but not limited to, the gene and promoter chosen, the condition, patient specific parameters, e.g., height, weight and age, and whether prevention or treatment is to be achieved. The gene therapy vector/device system of the invention is amenable to chronic use for prophylactic purposes.

Vectors of the invention may conveniently be provided in the form of formulations suitable for administration, e.g., into the blood stream (e.g., in an intracoronary artery). A suitable administration format may best be determined by a medical practitioner for each patient individually, according to standard procedures. Suitable pharmaceutically acceptable carriers and their formulation are described in standard formulations treatises, e.g., Remington's Pharmaceuticals Sciences. Vectors of the present invention should preferably be formulated in solution at neutral pH, for example, about pH 6.5 to about pH 8.5, more preferably from about pH 7 to 8, with an excipient to bring the solution to about isotonicity, for example, 4.5% mannitol or 0.9% sodium chloride, pH buffered with art-known buffer solutions, such as sodium phosphate, that are generally regarded as safe, together with an accepted preservative such as metacresol 0.1% to 0.75%, more preferably from 0.15% to 0.4% metacresol. Obtaining a desired isotonicity can be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions. If desired, solutions of the above compositions can also be prepared to enhance shelf life and stability. Therapeutically useful compositions of the invention can be prepared by mixing the ingredients following generally accepted procedures. For example, the selected components can be mixed to produce a concentrated mixture which may then be adjusted to the final concentration and viscosity by the addition of water and/or a buffer to control pH or an additional solute to control tonicity.

The vectors can be provided in a dosage form containing an amount of a vector effective in one or multiple doses. For viral vectors, the effective dose may be in the range of at least about $10^7$ viral particles, preferably about $10^9$ viral particles, and more preferably about $10^{11}$ viral particles. The number of viral particles may, but preferably does not exceed $10^{14}$. As noted, the exact dose to be administered is determined by the attending clinician, but is preferably in 1 ml phosphate buffered saline. For delivery of recombinant cells, the number of cells to be administered will be an amount which results in a beneficial effect to the recipient. For example, from $10^2$ to $10^{10}$, e.g., from $10^3$ to $10^9$, $10^4$ to $10^8$, or $10^5$ to $10^7$, cells can be administered. For delivery of plasmid DNA alone, or plasmid DNA in a complex with other macromolecules, the amount of DNA to be administered will be an amount which results in a beneficial effect to the recipient. For example, from 0.0001 to 1 mg or more, e.g., up to 1 g, in individual or divided doses, e.g., from 0.001 to 0.5 mg, or 0.01 to 0.1 mg, of DNA can be administered.

In one embodiment, in the case of heart disease, administration may be by intracoronary injection to one or both coronary arteries (or to one or more saphenous vein or internal mammary artery grafts or other conduits) using an appropriate coronary catheter. A variety of catheters and delivery routes can be used to achieve intracoronary delivery, as is known in the art. For example, a variety of general purpose catheters, as well as modified catheters, suitable for use in the present invention are available from commercial suppliers. Also, where delivery to the myocardium is achieved by injection directly into a coronary artery, a number of approaches can be used to introduce a catheter into the coronary artery, as is known in the art. By way of illustration, a catheter can be conveniently introduced into a femoral artery and threaded retrograde through the iliac artery and abdominal aorta and into a coronary artery. Alternatively, a catheter can be first introduced into a brachial or carotid artery and threaded retrograde to a coronary artery. Detailed descriptions of these and other techniques can be found in the art (see, e.g., above, including: Topol, (ed.), *The Textbook of Interventional Cardiology*, 4th Ed. (Elsevier 2002); Rutherford, *Vascular Surgery*, 5th Ed. (W. B. Saunders Co. 2000); Wyngaarden et al. (eds.), *The Cecil Textbook of Medicine*, 22nd Ed. (W. B. Saunders, 2001); and Sabiston, *The Textbook of Surgery*, 16th Ed. (Elsevier 2000)).

By way of illustration, liposomes and other lipid-containing gene delivery complexes can be used to deliver one or more transgenes. The principles of the preparation and use of such complexes for gene delivery have been described in the art (see, e.g., Ledley, *Human Gene Therapy*, 6:1129 (1995); Miller et al., *FASEB Journal*, 9:190 (1995); Chonn et al., *Curr. Opin. Biotech.*, 6:698 (1995); Schofield et al., *British Med. Bull.*, 51:56 (1995); Brigham et al., *J. Liposome Res.*, 3:31 (1993)).

Administration of the gene therapy vector in accordance with the present invention may be continuous or intermittent, depending, for example, upon the recipient's physiological condition, whether the purpose of the administration is therapeutic or prophylactic, and other factors known to skilled practitioners. The administration of the gene therapy vector may be essentially continuous over a preselected period of time or may be in a series of spaced doses. Both local and systemic administration is contemplated.

One or more suitable unit dosage forms comprising the gene therapy vector, which may optionally be formulated for sustained release, can be administered by a variety of routes including oral, or parenteral, including by rectal, buccal, vaginal and sublingual, transdermal, subcutaneous, intravenous, intramuscular, intraperitoneal, intrathoracic, intrapulmonary and intranasal routes. The formulations may, where appropriate, be conveniently presented in discrete unit dosage forms and may be prepared by any of the methods well known to pharmacy. Such methods may include the step of bringing into association the vector with liquid carriers, solid matrices, semi-solid carriers, finely divided solid carriers or combinations thereof, and then, if necessary, introducing or shaping the product into the desired delivery system.

Pharmaceutical formulations containing the gene therapy vector can be prepared by procedures known in the art using well known and readily available ingredients. For example, the agent can be formulated with common excipients, diluents, or carriers, and formed into tablets, capsules, suspensions, powders, and the like. The vectors of the invention can also be formulated as elixirs or solutions for convenient oral administration or as solutions appropriate for parenteral administration, for instance by intramuscular, subcutaneous or intravenous routes.

The pharmaceutical formulations of the vectors can also take the form of an aqueous or anhydrous solution or dispersion, or alternatively the form of an emulsion or suspension.

Thus, the vector may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint.

For administration to the upper (nasal) or lower respiratory tract by inhalation, the vector is conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the vector may be administered via nose drops, a liquid spray, such as via a plastic bottle atomizer or metered-dose inhaler. Typical of atomizers are the Mistometer (Wintrop) and the Medihaler (Riker).

The local delivery of the vectors can also be by a variety of techniques which administer the vector at or near the site of disease. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

For topical administration, the vectors may be formulated as is known in the art for direct application to a target area. Conventional forms for this purpose include wound dressings, coated bandages or other polymer coverings, ointments, creams, lotions, pastes, jellies, sprays, and aerosols, as well as in toothpaste and mouthwash, or by other suitable forms. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-25% by weight.

When desired, the above-described formulations can be adapted to give sustained release of the active ingredient employed, e.g., by combination with certain hydrophilic polymer matrices, e.g., comprising natural gels, synthetic polymer gels or mixtures thereof.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The vector may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; mouthwashes comprising the composition of the present invention in a suitable liquid carrier; and pastes and gels, e.g., toothpastes or gels, comprising the composition of the invention.

The formulations and compositions described herein may also contain other ingredients such as antimicrobial agents or preservatives.

Exemplary Vectors for Selected Conditions

In one embodiment, to inhibit or treat chronic heart failure (CHF), vectors are employed that encode gene products that improve calcium homeostatis and β-adenoreceptor function in cardiomyocytes. For instance, in one embodiment, to prevent, inhibit or treat CHF, a gene therapy vector, e.g., an adenoviral vector, which contains a Serca2A, phospholamban, β-AR, β-ARK1 inhibitor, V2 vasopressin receptor, or adenylyl cyclase-type VI gene operably linked to regulatable promoter is employed. The expression of such a gene in a mammal having CHF can enhance LV function, e.g., LV contactability. For example, to treat heart failure, a gene therapy vector having a regulatable transcriptional control element operably linked to an open reading frame for Serca2A is employed. In one embodiment, the regulatable transcriptional control element is regulated by a light sensitive promoter. After the gene therapy vector is administered to a mammal and an implanted device detects reduced cardiac function, e.g., decreased HRV, the device emits light of a wavelength or energy that activates the regulatable transcriptional control element in the gene therapy vector. Serca2A expression is then upregulated in an amount effective to increase cardiac performance. To inhibit apoptosis which may contribute to loss of cardiomyocytes and cardiac function in CHF, Bcl-2, Akt (protein kinase B), or phosphatidylionsitol-3 kinase may be employed in the same or different gene therapy vectors.

In another embodiment, to prevent, inhibit or treat atrial fibrillation, vectors are employed that contain genes for HSP, cardiomyocyte dedifferentiation, mink, a connexin, e.g., connexin 40, Serca2A, ryanodine receptor, proBNP, NPR-A, or one of Kir2.1-2.4. In particular, the inward rectifier potassium current ($I_{K1}$) is notable for its intense expression in electrically quiescent atria and ventricle, but not in nodal pacemaker cells. $I_{K1}$, encoded by the Kir2 gene family, stabilizes a strongly negative resting potential and may suppress excitability.

Thus, one embodiment, to treat atrial fibrillation, a gene therapy vector having a thermal sensitive transcriptional control element is linked to an open reading frame which encodes a gene product which alters the amount or activity of $I_{K1}$. After the gene therapy vector is administered to a mammal and an implanted device detects atrial fibrillation, e.g., by an electrogram, the device emits a thermal signal so as to increase expression of the gene product in an amount effective to alter the amount or activity of $I_{K1}$ After a predetermined time, or when the device detects the absence of atrial fibrillation, the thermal signal is terminated.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A system, comprising:
    an implantable gene regulatory signal delivery device that emits, in response to a gene regulatory control signal, a regulatory signal which regulates transcription from a regulatable transcriptional control element;
    an implantable cardiac rhythm management (CRM) device including:
        a sensor to sense a physiological signal indicative of a predetermined cardiac condition;
        an event detector configured to detect the predetermined cardiac condition from the sensed physiological signal and produce one or more condition parameters related to one of a type and a degree of the predetermined cardiac condition;
        and
        a controller coupled to the sensor and electrically connected to the gene regulatory signal delivery device, the controller configured to produce the gene regulatory control signal, transmit the gene regulatory signal to the gene regulatory signal delivery device to trigger an emission of the regulatory signal in response to a detection of the predetermined cardiac condition, and quantitatively control the emission of the regulatory signal based on the one or more condition parameters; and
    one or more implantable leads providing for electrical connections between the implantable gene regulatory signal delivery device and the implantable CRM device,
    wherein the controller is electrically wired to the gene regulatory signal delivery device through the electrical connections, and
    wherein the regulatory signal is selected to regulate the regulatable transcriptional control element in a vector having the regulatable transcriptional control element operably linked to an open reading frame, the expression of which treats the predetermined cardiac condition.

2. The system of claim 1, wherein the gene regulatory signal delivery device comprises an electric field generator which emits an electric field as the gene regulatory signal.

3. The system of claim 1, wherein the gene regulatory signal delivery device comprises an electromagnetic field generator which emits an electromagnetic field as the gene regulatory signal.

4. The system of claim 1, wherein the gene regulatory signal delivery device comprises a light emitter which emits a light having a predetermined wavelength and energy.

5. The system of claim 1, wherein the gene regulatory signal delivery device comprises a speaker which emits an acoustic energy.

6. The system of claim 1, wherein the gene regulatory signal delivery device comprises a drug delivery device which contains a chemical agent.

7. The system of claim 1, wherein the gene regulatory signal delivery device comprises a thermal radiator which emits a thermal energy.

8. The system of claim 1, wherein the sensor comprises an electrogram sensing circuit, and the event detector comprises an arrhythmia detector.

9. The system of claim 8, wherein the event detector comprises an atrial fibrillation detector.

10. The system of claim 8, wherein the event detector comprises a ventricular fibrillation detector.

11. The system of claim 1, wherein the sensor comprises a sensor sensing a physiological signal indicative of ischemia, and the event detector comprises an ischemia detector.

12. The system of claim 1, wherein the sensor comprises a metabolic sensor adapted to sense a signal indicative of a cardiac metabolic level.

13. The system of claim 12, wherein the sensor comprises at least one of a pH sensor, an oxygen pressure ($PO_2$) sensor, a carbon dioxide pressure ($PCO_2$) sensor, a glucose sensor, a creatine sensor, a C-creative protein sensor, a creatine kinase sensor, and a creatine kinase-MB sensor.

14. The system of claim 1, wherein the sensor comprises an impedance sensor to sense tissue impedance.

15. The system of claim 14, wherein the impedance sensor comprises a pulmonary impedance sensor.

16. The system of claim 15, wherein the impedance sensor comprises a respiratory sensor.

17. The system of claim 1, wherein the sensor comprises a pressure sensor to sense a pressure in a cardiovascular system.

18. The system of claim 17, wherein the pressure sensor comprises at least one of a left atrial pressure sensor, a left ventricular pressure sensor, an artery pressure sensor, and a pulmonary arterial pressure sensor.

19. The system of claim 18, wherein the event detector comprises a systolic dysfunction detector.

20. The system of claim 18, wherein the event detector comprises a diastolic dysfunction detector.

21. The system of claim 1, wherein the sensor comprises a stroke volume sensor.

22. The system of claim 1, wherein the sensor comprises a neural activity sensor.

23. The system of claim 22, wherein the neural activity sensor comprises a neurohormone sensor to sense a neurohormone level.

24. The system of claim 22, wherein the neural activity sensor comprises an action potential recorder to sense neural electrical activities.

25. The system of claim 1, wherein the sensor comprises a heart rate variability detector.

26. The system of claim 1, wherein the sensor comprises a renal function sensor.

27. The system of claim 26, wherein the renal function sensor comprises at least one of a renal output sensor, a filtration rate sensor, and an angiotensin II level sensor.

28. The system of claim 1, wherein the sensor comprises an acoustic sensor adapted to sense at least one of heart sounds and respiratory sounds.

29. The system of claim 28, wherein the event detector to detect the predetermined cardiac condition when third heart sound (S3) amplitude exceeds a predetermined threshold.

30. The system of claim 1, wherein the controller is adapted to quantitatively control the emission of the regulatory signal using parameters defining type and energy of the regulatory signal.

31. A system, comprising:
an implantable gene regulatory signal delivery device that emits, in response to a gene regulatory control signal, a regulatory signal which regulates transcription from a regulatable transcriptional control element; and
an implantable medical device system including:
a sensor to sense a physiological signal indicative of a predetermined cardiac condition;
an event detector configured to detect the predetermined cardiac condition from the sensed physiological signal and produce one or more condition parameters related to at least one of a type and a degree of the predetermined cardiac condition;
an implant telemetry module to receive an external command;
and
an implant controller coupled to the sensor and the implant telemetry module, the implant controller configured to quantitatively control the emission of the regulatory signal based on the one or more condition parameters and the external command;
one or more implantable leads providing for electrical connections between the implantable gene regulatory signal delivery device and the implantable medical device, wherein the implant controller is electrically wired to the gene regulatory signal delivery device through the electrical connections; and
an external system including:
an external telemetry module to transmit the external command to the implant telemetry module;
a user input device adapted to receive the external command; and
an external controller adapted to automatically analyze signals acquired by the implantable medical device and generate the external command when deemed necessary as a result of the analysis,
wherein the regulatory signal is selected to regulate a regulatable transcriptional control element in a vector having the regulatable transcriptional control element operably linked to an open reading frame, the expression of which in an effective amount treats the predetermined cardiac condition.

32. The system of claim 31, wherein the gene regulatory signal delivery device comprises an electric field generator which emits an electric field being the regulatory signal.

33. The system of claim 31, wherein the gene regulatory signal delivery device comprises an electromagnetic generator which emits an electromagnetic field as the gene regulatory signal.

34. The system of claim 31, wherein the gene regulatory signal delivery device comprises a light emitter which emits a light having a predetermined wavelength and energy.

35. The system of claim 31, wherein the gene regulatory signal delivery device comprises a speaker which emits an acoustic energy.

36. The system of claim 31, wherein the gene regulatory signal delivery device comprises a drug delivery device which contains a chemical agent.

37. The system of claim 31, wherein the gene regulatory signal delivery device comprises a thermal radiator which emits a thermal energy.

38. The system of claim 31, wherein the sensor comprises an electrogram sensing circuit, and the event detector comprises an arrhythmia detector.

39. The system of claim 38, wherein the event detector comprises an atrial fibrillation detector.

40. The system of claim 38, wherein the event detector comprises a ventricular fibrillation detector.

41. The system of claim 31, wherein the sensor comprises a sensor sensing an physiological signal indicative of ischemia, and the event detector comprises an ischemia detector.

42. The system of claim 31, wherein the sensor comprises a metabolic sensor adapted to sense a signal indicative of a cardiac metabolic level.

43. The system of claim 42, wherein the sensor comprises at least one of a pH sensor, an oxygen pressure ($PO_2$) sensor, a carbon dioxide pressure ($PCO_2$) sensor, a glucose sensor, a creatine sensor, a C-creative protein sensor, a creatine kinase sensor, and a creatine kinase-MB sensor.

44. The system of claim 31, wherein the sensor comprises an impedance sensor to sense tissue impedance.

45. The system of claim 44, wherein the impedance sensor comprises a pulmonary impedance sensor.

46. The system of claim 45, wherein the impedance sensor comprises a respiratory sensor.

47. The system of claim 31, wherein the sensor comprises a pressure sensor to sense a pressure in a cardiovascular system.

48. The system of claim 47, wherein the pressure sensor comprises at least one of a left atrial pressure sensor, a left ventricular pressure sensor, an artery pressure sensor, and a pulmonary arterial pressure sensor.

49. The system of claim 48, wherein the event detector comprises a systolic dysfunction detector.

50. The system of claim 48, wherein the event detector comprises a diastolic dysfunction detector.

51. The system of claim 31, wherein the sensor comprises a stroke volume sensor.

52. The system of claim 31, wherein the sensor comprises a neural activity sensor.

53. The system of claim 52, wherein the neural activity sensor comprises a neurohormone sensor to sense a neurohormone level.

54. The system of claim 52, wherein the neural activity sensor comprises an action potential recorder to sense neural electrical activities.

55. The system of claim 31, wherein the sensor comprises a heart rate variability detector.

56. The system of claim 31, wherein the sensor comprises a renal function sensor.

57. The system of claim 56, wherein the renal function sensor comprises at least one of a renal output sensor, a filtration rate sensor, and an angiotensin II level sensor.

58. The system of claim 31, wherein the sensor comprises an acoustic sensor adapted to sense at least one of heart sounds and respiratory sounds.

59. The system of claim 58, wherein the event detector to detect the predetermined cardiac condition when third hear sound (S3) amplitude or activity exceeds a predetermined threshold level.

60. The system of claim 31, wherein the implantable medical device system further comprises a pacing circuit coupled to the implant controller, and wherein the implant controller includes a pacing control module adapted to control a delivery of pacing pulses in conjunction with the emission of the regulatory signal.

61. The system of claim 60, wherein the pacing control module is further adapted to control the delivery of pacing pulses based on at least the external command.

62. The system of claim 60, wherein the implantable medical device system further comprises a cardiac resynchronization therapy (CRT) circuit coupled to the implant controller, and wherein the implant controller includes a CRT control module adapted to control a delivery of CRT in conjunction with the emission of the regulatory signal.

63. The system of claim 60, wherein the implantable medical device system further comprises a remodeling control (RCT) therapy circuit coupled to the implant controller, and wherein the implant controller includes a RCT therapy control module adapted to control a delivery of RCT therapy in conjunction with the emission of the regulatory signal.

64. The system of claim 60, wherein the implantable medical device system further comprises a defibrillation circuit coupled to the implant controller, and wherein the implant controller includes a defibrillation control module adapted to control a delivery of cardioversion/defibrillation shocks in conjunction with the emission of the regulatory signal.

65. The system of claim 64, wherein the defibrillation control module is further adapted to control the delivery of cardioversion/defibrillation shocks based on at least the external command.

66. The system of claim 64, further comprising at least one atrial defibrillation lead coupled to the defibrillation circuit to deliver the defibrillation shocks to one or more atria, and wherein the defibrillation control module comprises an atrial defibrillation control module.

67. The system of claim 64, further comprising at least one ventricular defibrillation lead coupled to the defibrillation circuit to deliver the defibrillation shocks to one or more ventricles, and wherein the defibrillation control module comprises a ventricular defibrillation control module.

68. The system of claim 31, wherein the implantable medical device system comprises a hermetically sealed can to house at least the implant controller and the implant telemetry module.

69. The system of claim 68, wherein the hermetically sealed can further houses the sensor.

70. The system of claim 68, wherein the sensor is external to the hermetically sealed can.

71. The system of claim 31, wherein the external system comprises:
a presentation device to present the sensed physiological signal; and
a user input device to receive the external command.

72. The system of claim 71, wherein the external system comprises a programmer.

73. The system of claim 71, wherein the external system comprises an advanced patient management system including:
an external device wirelessly coupled to the implantable medical device system via telemetry;
a remote device to provide for access to the implantable medical device system from a distant location; and
a network connecting the external device and the remote device.

74. The system of claim 73, wherein the external device comprises the user input.

75. The system of claim 73, wherein the remote device comprises the user input.

76. The system of claim 1 or 31 wherein the vector is not part of an implantable device.

77. The system of claim 1 or 31 wherein the controller comprises a timer adapted to time a predetermined period of delivery time during which the gene regulatory signal delivery device emits the regulatory signal.

* * * * *